United States Patent
Murase et al.

(10) Patent No.: US 7,993,888 B2
(45) Date of Patent: Aug. 9, 2011

(54) BACTERIUM HAVING ENHANCED 2-OXOGLUTARATE DEHYDROGENASE ACTIVITY

(75) Inventors: Makoto Murase, Yokohama (JP); Ryusuke Aoyama, Yokohama (JP); Akiko Sakamoto, Yokohama (JP); Sanae Sato, Yokohama (JP); Madoka Yonekura, Yokohama (JP); Shuichi Yunomura, Yokohama (JP); Kenji Yamagishi, Yokohama (JP); Keita Fukui, Kawasaki (JP); Chie Koseki, Kawasaki (JP); Jun Nakamura, Kawasaki (JP); Hiroyuki Kojima, Kawasaki (JP)

(73) Assignees: Mitsubishi Chemical Corporation, Tokyo (JP); Ajinomoto Co., Inc., Tokyo (JP)

( * ) Notice: Subject to any disclaimer, the term of this patent is extended or adjusted under 35 U.S.C. 154(b) by 180 days.

(21) Appl. No.: 12/280,426

(22) PCT Filed: Feb. 23, 2007

(86) PCT No.: PCT/JP2007/053360
§ 371 (c)(1),
(2), (4) Date: Dec. 9, 2008

(87) PCT Pub. No.: WO2007/099867
PCT Pub. Date: Sep. 7, 2007

(65) Prior Publication Data
US 2009/0156779 A1    Jun. 18, 2009

(30) Foreign Application Priority Data
Feb. 24, 2006  (JP) .................................. 2006-048060

(51) Int. Cl.
C12P 7/46    (2006.01)
C12P 21/06   (2006.01)
C12N 1/20    (2006.01)
C12N 15/00   (2006.01)
C12N 9/04    (2006.01)
C07H 21/02   (2006.01)
C07H 21/04   (2006.01)
C08G 63/02   (2006.01)

(52) U.S. Cl. ................... 435/145; 435/252.32; 435/69.1; 435/320.1; 435/190; 536/23.1; 536/23.2; 528/272

(58) Field of Classification Search .................. 435/145, 435/252.32, 69.1, 320.1, 190; 536/23.1, 536/23.2; 528/272
See application file for complete search history.

(56) References Cited

U.S. PATENT DOCUMENTS

| | | |
|---|---|---|
| 4,489,160 A | 12/1984 | Katsumata et al. |
| 4,500,640 A | 2/1985 | Katsumata et al. |
| 4,514,502 A | 4/1985 | Miwa et al. |
| 4,617,267 A | 10/1986 | Katsumata et al. |
| 5,034,105 A | 7/1991 | Berglund et al. |
| 5,132,456 A | 7/1992 | King et al. |
| 5,142,834 A | 9/1992 | Laclave et al. |
| 5,143,833 A | 9/1992 | Datta |
| 5,143,834 A | 9/1992 | Glassner et al. |
| 5,168,055 A | 12/1992 | Datta et al. |
| 5,185,262 A | 2/1993 | Kohama et al. |
| 5,504,004 A | 4/1996 | Guettler et al. |
| 5,770,435 A | 6/1998 | Donnelly et al. |
| 5,827,700 A | 10/1998 | Felman et al. |
| 5,869,301 A | 2/1999 | Nghiem et al. |
| 5,958,744 A | 9/1999 | Berglund et al. |
| 5,977,331 A | 11/1999 | Asakura et al. |
| 6,265,190 B1 | 7/2001 | Yedur et al. |
| 6,448,061 B1 | 9/2002 | Pan et al. |
| 6,455,284 B1 | 9/2002 | Gokarn et al. |
| 6,696,561 B1 | 2/2004 | Pompejus et al. |
| 2002/0055152 A1 | 5/2002 | Farwick et al. |
| 2002/0150999 A1 | 10/2002 | Dusch et al. |
| 2002/0197605 A1 | 12/2002 | Nakagawa et al. |
| 2003/0017559 A1 | 1/2003 | Donnelly et al. |
| 2003/0069354 A1 | 4/2003 | Oyasato et al. |
| 2003/0087381 A1 | 5/2003 | Gokarn et al. |
| 2003/0100079 A1 | 5/2003 | Mockel et al. |
| 2004/0152159 A1* | 8/2004 | Causey et al. ................ 435/69.1 |
| 2005/0196848 A1 | 9/2005 | Dusch et al. |
| 2006/0046288 A1 | 3/2006 | Ka-Yiu et al. |
| 2006/0073577 A1 | 4/2006 | Ka-Yiu et al. |
| 2006/0172401 A1 | 8/2006 | Yamagishi |
| 2006/0205048 A1 | 9/2006 | Murase et al. |
| 2006/0228712 A1 | 10/2006 | Nakagawa et al. |
| 2006/0276674 A1 | 12/2006 | Kushiku et al. |
| 2006/0281156 A1 | 12/2006 | Aoyama et al. |
| 2007/0087423 A1 | 4/2007 | Murakami et al. |
| 2007/0154999 A1 | 7/2007 | Fukui et al. |
| 2008/0293112 A1 | 11/2008 | Fukui et al. |

(Continued)

FOREIGN PATENT DOCUMENTS
CA    2322553    4/2001
(Continued)

OTHER PUBLICATIONS

Darlison et al., "Nucleotide sequence of the *sucA* gene encoding the 2-oxoglutarate dehydrogenase of *Escherichia coli* K12," Eur. J. Biochem., vol. 141, No. 2, pp. 351-359, XP000872318, ISSN: 0014-2956, Jun. 1, 1984.

(Continued)

Primary Examiner — Ganapathirama Raghu
(74) Attorney, Agent, or Firm — Greenblum & Bernstein, P.L.C.

(57) ABSTRACT

Provided is a bacterium which is capable of producing an organic acid and is modified so as to have an enhanced 2-oxoglutarate dehydrogenase activity as compared with that of an unmodified strain. An organic acid such as succinic acid can be produced by culturing the bacterium.

6 Claims, 2 Drawing Sheets

U.S. PATENT DOCUMENTS

2008/0293113 A1    11/2008    Koseki et al.

FOREIGN PATENT DOCUMENTS

| | | |
|---|---|---|
| EP | 0075612 | 4/1983 |
| EP | 0078537 | 5/1983 |
| EP | 0389103 | 9/1990 |
| EP | 0410728 | 1/1991 |
| EP | 1096013 | 5/2001 |
| EP | 1108790 | 6/2001 |
| EP | 1672077 | 6/2006 |
| EP | 1748062 | 1/2007 |
| JP | 57-134500 | 8/1982 |
| JP | 57-183799 | 11/1982 |
| JP | 58-35197 | 3/1983 |
| JP | 58-67679 | 4/1983 |
| JP | 58-77895 | 5/1983 |
| JP | 58-192900 | 11/1983 |
| JP | 61-209596 | 9/1986 |
| JP | 62-048394 | 3/1987 |
| JP | 62-238231 | 10/1987 |
| JP | 62-238232 | 10/1987 |
| JP | 62-294090 | 12/1987 |
| JP | 1-191686 | 8/1989 |
| JP | 2-072876 | 3/1990 |
| JP | 2-283289 | 11/1990 |
| JP | 3-072891 | 3/1991 |
| JP | 3-151884 | 6/1991 |
| JP | 3-210184 | 9/1991 |
| JP | 5-260985 | 10/1993 |
| JP | 6-014781 | 1/1994 |
| JP | 7-067683 | 3/1995 |
| JP | 7-304839 | 11/1995 |
| JP | 11-113588 | 4/1999 |
| JP | 11-130852 | 5/1999 |
| JP | 11-196887 | 7/1999 |
| JP | 11-196888 | 7/1999 |
| JP | 11-206385 | 8/1999 |
| JP | 2000-500333 | 1/2000 |
| JP | 2000-037196 | 2/2000 |
| JP | 2001-161386 | 6/2001 |
| JP | 2001-190297 | 7/2001 |
| JP | 2001-514900 | 9/2001 |
| JP | 2002-511250 | 4/2002 |
| JP | 2002-191370 | 7/2002 |
| JP | 2002-291477 | 10/2002 |
| JP | 2003-171448 | 6/2003 |
| JP | 2003-199522 | 7/2003 |
| JP | 2003-235592 | 8/2003 |
| JP | 2003-235593 | 8/2003 |
| JP | 2005-095169 | 4/2005 |
| JP | 2006-238843 | 9/2006 |
| JP | 2006-320208 | 11/2006 |
| JP | EP1748062 A1 * | 3/2007 |
| JP | EP1760143 A1 * | 3/2007 |
| WO | 95/34672 | 12/1995 |
| WO | 97/16528 | 5/1997 |
| WO | 99/06532 | 2/1999 |
| WO | 99/09196 | 2/1999 |
| WO | 99/53035 | 10/1999 |
| WO | 01/66508 | 9/2001 |
| WO | 02/29020 | 4/2002 |
| WO | 02/36797 | 5/2002 |
| WO | 02/072855 | 9/2002 |
| WO | 03/040290 | 5/2003 |
| WO | 2005/005649 | 1/2005 |
| WO | 2005/010182 | 2/2005 |
| WO | 2005/021770 | 3/2005 |
| WO | 2005/026349 | 3/2005 |
| WO | 2005/030973 | 4/2005 |
| WO | 2005/113744 | 12/2005 |
| WO | 2005/113745 | 12/2005 |
| WO | 2006/020663 | 2/2006 |
| WO | 2006/031424 | 3/2006 |
| WO | 2006/034156 | 3/2006 |
| WO | 2006/069174 | 6/2006 |
| WO | 2007/046389 | 4/2007 |
| WO | 2007/099867 | 9/2007 |

OTHER PUBLICATIONS

Sanchez et al., "Efficient succinic acid production from glucose through overexpression of pyruvate carboxylase in an *Escherichia coli* alcohol dehydrogenase and lactate dehydrogenase mutant," Biotechnol. Prog., vol. 21, No. 2, pp. 358-365, XP002391565, ISSN: 8756-7938, Mar. 2, 2005.
Extended European Search Report dated Feb. 24, 2010 that issued with respect to patent family member European Patent Application No. 07714831.0.
Arikawa et al. *J Biosci. Bioeng.* 87(1):28-36, 1999.
Ba et al. *Biomacromolecules* 4:1827-1834, 2003.
Bott et al. *Journal of Biotechnology* 104:129-153, 2003.
Branden et al. *Introduction to Protein Structure*, Garland Publishing Inc., New York, p. 247, 1991.
Calvary et al. *Microchemical Journal* 23(4):473-480, 1978.
Chang et al. *J. Bacteriol.* 151:1279-1289, 1982.
Chotani et al. *Biochimica et Biophysica Acta, Protein Structure and Molecular Enzymology*, 1543(2):434-455, 2000.
Database UniProt, Accession No. Q8NMK4, Oct. 1, 2002.
Database EPO Proteins, Accession No. AX771820, Jul. 2, 2003.
Database EMBL, Accession No. AX771819, Jul. 2, 2003.
Database Geneseq, Accession No. AAG92572, Sep. 26, 2001.
Database EMBL, Accession No. AX122910, May 10, 2001.
Database UniProt, Accession No. Q6M2R3, Jul. 5, 2004.
Dunn et al. *J. Bacteriol.* 178:5960-5970, 1996.
Gergely et al. *J. Biol. Chem.* 198:323-334, 1952.
Gokarn et al. *Biotechnology Letters* 20(8):795-798, 1998.
Gokarn et al. *Applied and Environmental Microbiology* 66(5):1844-1850, 2000.
Gokarn et al. *Appl. Microbiol. Biotechnol.* 56:188-195, 2001.
Goldberg et al. *Applied and Environmental Microbiology* 45(6):1838-1847, 1983.
Gong et al. *Applied Biochemistry and Biotechnology* 57/58:481-487, 1996.
Guettler et al. *International Journal of Systematic Bacteriology* 49:207-216, 1999.
Hong et al. *Biotechnology and Bioengineering* 74(2):89-95, 2001.
Hong et al. *Applied Microbiology and Biotechnology* 58:286-290, 2002.
Imabori et al. "Seikagaku Jiten" Dai 3 Pan Tokyo Kagaku Dojin, Oct. 8, 1998, p. 329-333.
Inui et al. *J. of Mol. Microbiol. and Biotech.* 7(4):182-196, 2004.
Jaurin et al. GenBank accession No. J01611, Feb. 2000.
Kalinowski et al. *J. of Biotech.* 104(1-3):5-25, 2003.
Kanarek et al. *J. Biol. Chem.* 239:4202-4206, 1964.
KEGG Database on-line, NCgl0359, 2006.
KEGG Database on-line, NCgl0360, 2006.
KEGG Database on-line, NCgl0361, 2006.
Kirchner et al. *J. of Biotech.* 104(1-3):287-299, 2003.
Klotzsch et al., *Meth. Enzymol.* 12:381-386, 1969.
Kondo et al. *Gene* 191:47-50, 1997.
Kurokawa et al. *Arch. Microbiol.* 183:317-324, 2005.
Lehn et al. *Gene* 165:331-332, 1995.
Liebl et al. *International Journal of Systemic Bacteriology* 41:255-260, 1991.
Lin et al. *Applied Genetics and Molecular Biotechnology*, published online: Nov. 24, 2004, total pp. 16.
Mackay et al. *Biochem. Biophys. Res. Comm.* 202:1009-1014, 1994.
Mat-Jan et al. *Journal of Bacteriology* 171(1):342-348, 1989.
Maxa et al. *Mitteilungen Klosterneuburg* 41(6):223-237, 1991.
Millard et al. *Applied and Environmental Microbiology* 62(5):1808-1810, 1996.
Mori et al. *Shokuhin to Kagaku* 44(4):43-49, 2002.
Peters-Windisch et al. *Microbiology* 144:915-927, 1998.
Ramponi, *Meth. Enzymol.* 42:409-426, 1975.
Reinscheid et al. *Microbiology* 145:503-513, 1999.
Schafer et al., *Gene* 145:69-73, 1994.
Schnorpfeil et al. *Eur. J. Biochem.* 268:3069-3074, 2001.
Seffernick et al. *J. Bacteriol.* 183(8):2405-2410, 2001.
Shiio et al. *Agric. Biol. Chem.* 44(8):1897-1904, 1980.
Song et al. *Enzyme Microbiol. Technol.* 309:352-361, 2006.

Stols et al. *Applied and Environmental Microbiology* 63(7):2695-2701, 1997.
Stucka et al. *Mol. Gen. Genet.* 229:307-315, 1991.
Tomar et al. *Appl. Microbiol. Biotechnol.* 62:76-82, 2003.
Torino et al. *J. Appl. Microbiol.* 91:846-852, 2001.
Uematsu et al. *Plant Cell Reports* 10:286-290, 1991.
Usuda et al. *Microbiology* 142:3347-3354, 1996.
Vertes et al. *Res. Microbiol.* 144:181-185, 1993.
Wang et al. *Applied Biochemistry and Biotechnology* 70-72:919-928, 1998.
Whisstock et al. *Q. Rev. Biophysics* 36(3):307-340, 2003.
Witkowski et al. *Biochemistry* 38:11643-11650, 1999.
Zeikus et al. *Appl. Microbiol. Biotechnol.* 51:545-552, 1999.
Zhang et al. *Proc. Natl. Acad. Sci. USA* 90:1766-1770, 1993.
Klotzsch, *Meth. Enzymol.* 12:381-386, 1969.
English Language Abstract of JP 1-191686, Aug. 1, 1989.
English Language Abstract of JP 2-072876, Mar. 13, 1990.
English Language Abstract of JP 3-072891, Mar. 28, 1991.
English Language Abstract of JP 3-210184, Sep. 13, 1991.
English Language Abstract of JP 5-260985, Oct. 12, 1993.
English Language Abstract of JP 6-014781, Jan. 25, 1994.
English Language Abstract of JP 7-067683, Mar. 14, 1995.
English Language Abstract of JP 7-304839, Nov. 21, 1995.
English Language Abstract of JP 11-113588, Apr. 27, 1999.
English Language Abstract of JP 11-130852, May 18, 1999.
English Language Abstract of JP 11-196887, Jul. 27, 1999.
English Language Abstract of JP 11-196888, Jul. 27, 1999.
English Language Abstract of JP 11-206385, Aug. 3, 1999.
English Language Abstract of JP 57-134500, Aug. 19, 1982.
English Language Abstract of JP 57-183799, Nov. 12, 1982.
English Language Abstract of JP 58-035197, Mar. 1, 1983.
English Language Abstract of JP 58-077895, May 11, 1983.
English Language Abstract of JP 58-192900, Nov. 10, 1983.
English Language Abstract of JP 61-209596, Sep. 17, 1986.
English Language Abstract of JP 62-048394, Mar. 3, 1987.
English Language Abstract of JP 62-238231, Oct. 19, 1987.
English Language Abstract of JP 62-238232, Oct. 19, 1987.
English Language Abstract of JP 2000-037196, Feb. 8, 2000.
English Language Abstract of JP 2001-161386, Jun. 19, 2001.
English Language Abstract of JP 2001-190297, Jul. 17, 2001.
English Language Abstract of JP 2002-191370, Jul. 9, 2002.
English Language Abstract of JP 2002-291477, Oct. 8, 2002.
English Language Abstract of JP 2003-171448, Jun. 20, 2003.
English Language Abstract of JP 2003-199522, Jul. 15, 2003.
English Language Abstract of JP 2003-235592, Aug. 26, 2003.
English Language Abstract of JP 2003-235593, Aug. 26, 2003.
English Language Abstract of JP 2005-095169, Apr. 14, 2005.
English Language Abstract of JP 2006-238843, Sep. 14, 2006.
English Language Abstract of JP 2006-320208, Nov. 30, 2006,.
NP_601767, NCBI Sequence Viewer, Acetyl-CoA hydrolase, locus field date: Dec. 14, 2006.
NP_601811, NCBI Sequence Viewer, Pyruvate Dehyrogenase, locus field date: Dec. 14, 2006.
International Search Report for PCT/JP2007/053360, mailed May 29, 2007.

\* cited by examiner

BACTERIUM HAVING ENHANCED 2-OXOGLUTARATE DEHYDROGENASE ACTIVITY

TECHNICAL FIELD

The present invention relates to an organic acid-producing bacterium such as a coryneform bacterium, and relates to production of an organic acid such as succinic acid using the organic acid-producing bacterium.

BACKGROUND ART

For production of organic acids including succinic acid by fermentation, anaerobic bacteria such as those belonging to the genus *Anaerobiospirillum* and the genus *Actinobacillus* are usually used (Patent Documents 1 and 2, and Non-Patent Document 1). Use of anaerobic bacteria makes yields of products high, while demanding many nutrients for the proliferation of the anaerobic bacteria. Therefore, it is necessary to add a large amount of an organic nitrogen source such as corn steep liquor (CSL) in a medium. The abundant addition of the organic nitrogen source not only leads to an increase in cost of the medium but also leads to an increase in cost of purification for isolating the product, thereby resulting in being uneconomical.

In addition, a method in which aerobic bacteria such as coryneform bacteria are first cultured under an aerobic condition to proliferate the bacteria, and then, the bacteria are kept under anaerobic conditions as resting bacteria to produce an organic acid has also been known (Patent Documents 3 and 4). In this case, for proliferating bacterial cells, only a small amount of organic nitrogen is added, so this method is economical because the bacterial cells can grow sufficiently in a simple medium, but still to be improved in terms of the amount of produced organic acid of interest, the concentration thereof, and the production rate thereof per bacterial cell as well as simplification of the production method, and the like. In addition, fermentative production of an organic acid using a bacterium in which phosphoenolpyruvate carboxylase activity is enhanced has been reported (such as Patent Document 5), but further development of fermentative production for an organic acid has been demanded.

It has been reported that 2-oxoglutarate dehydrogenase (also called α-ketoglutarate dehydrogenase) activity was detected in a coryneform bacterium (Non-Patent Document 2), and the gene of 2-oxoglutarate dehydrogenase was cloned (Non-Patent Document 3). In addition, there is disclosed a production method for an amino acid using a microorganism in which 2-oxoglutarate dehydrogenase activity has been decreased (Patent Document 6).

However, producing an organic acid using a bacterium in which 2-oxoglutarate dehydrogenase activity is enhanced has not been reported so far.

Patent Document 1: U.S. Pat. No. 5,143,834
Patent Document 2: U.S. Pat. No. 5,504,004
Patent Document 3: JP-A-11-113588
Patent Document 4: JP-A-11-196888
Patent Document 5: JP-A-11-196887
Patent Document 6: WO 95/34672
Non-Patent Document 1: International Journal of Systematic Bacteriology (1999), 49, 207-216
Non-Patent Document 2: Shiio I, Ujigawa-Takeda K. 1980. Presence and regulation of α-ketoglutarate dehydrogenase complex in a glutamate-producing bacterium, *Brevibacterium Flavum*. Agric. Biol. Chem. 44: 1897-1904.
Non-Patent Document 3: Usuda Y, Tujimoto N, Abe C, Asakura Y, Kimura E, Kawahara Y, 0, Matsui H.1996. Molecular cloning of the *Corynebacterium glutamicum* ('*Brevibacterium lactofermentum*' AJ12036) odhA gene encoding a novel type of 2-oxoglutaratedehydrogenase. Microbiology. 142: 3347-54.

DISCLOSURE OF THE INVENTION

An object of the present invention is to provide a method of producing an organic acid such as succinic acid with higher production efficiency.

The inventors of the present invention have intensively studied to solve the above-mentioned object. As a result, the inventors found that, by allowing a bacterium modified so that 2-oxoglutarate dehydrogenase activity is enhanced or a treated cell thereof to act on an organic raw material in a reaction solution containing an carbonate ion, a bicarbonate ion, or carbon dioxide gas, the consumption rate of the organic raw material, the production rate of an organic acid such as succinic acid, or the yield of the organic acid is increased, whereby the present invention has been completed.

That is, the present invention provides the followings.

(1) A bacterium having an organic acid-producing ability, wherein said bacterium is modified so that 2-oxoglutarate dehydrogenase activity is enhanced as compared with an 2-oxoglutarate dehydrogenase-unmodified strain.

(2) A bacterium having an organic acid-producing ability, wherein said bacterium is modified so that acetic acid production is decreased, and 2-oxoglutarate dehydrogenase activity is enhanced as compared with a 2-oxoglutarate dehydrogenase-unmodified strain.

(3) The bacterium according to (2), wherein acetic acid production is decreased by decreasing one of or both of acetate kinase activity and phosphotransacetylase activity.

(4) The bacterium according to (2), wherein acetic acid production is decreased by decreasing acetyl-CoA hydrolase activity.

(5) The bacterium according to (2), wherein acetic acid production is decreased by decreasing pyruvate oxidase activity.

(6) The bacterium according to any one of (1) to (5), wherein the bacterium is further modified so that lactate dehydrogenase activity is decreased.

(7) The bacterium according to any one of (1) to (6), wherein the bacterium is further modified so that pyruvate carboxylase activity is enhanced.

(8) The bacterium according to any one of (1) to (7), wherein the bacterium is selected from the group consisting of a coryneform bacterium, a *Bacillus* bacterium, a *Rhizobium* bacterium, an *Escherichia* bacterium, a *Lactobacillus* bacterium, and a *Saccinobacillus* bacterium.

(9) The bacterium according to any one of (1) to (8), wherein the organic acid is succinic acid.

(10) A method for producing an organic acid, comprising:
allowing the bacterium according to any one of (1) to (9) or a treated cell thereof to act on an organic raw material in a reaction solution containing a carbonate ion, a bicarbonate ion, or carbon dioxide gas to thereby produce an organic acid; and
collecting the organic acid.

(11) The method according to (10), wherein the bacterium or the treated cell thereof is allowed to act on an organic raw material under anaerobic atmosphere.

(12) The method according to (10) or (11), wherein the organic raw material is glucose or sucrose.

(13) The method according to any one of (10) to (12), wherein the organic acid is succinic acid.

(14) A method for producing an organic acid-containing polymer, comprising:

producing an organic acid by the method according to any one of (10) to (13); and subjecting the obtained organic acid as a raw material to a polymerization reaction.

BEST MODE FOR CARRYING OUT THE INVENTION

Figure 1:
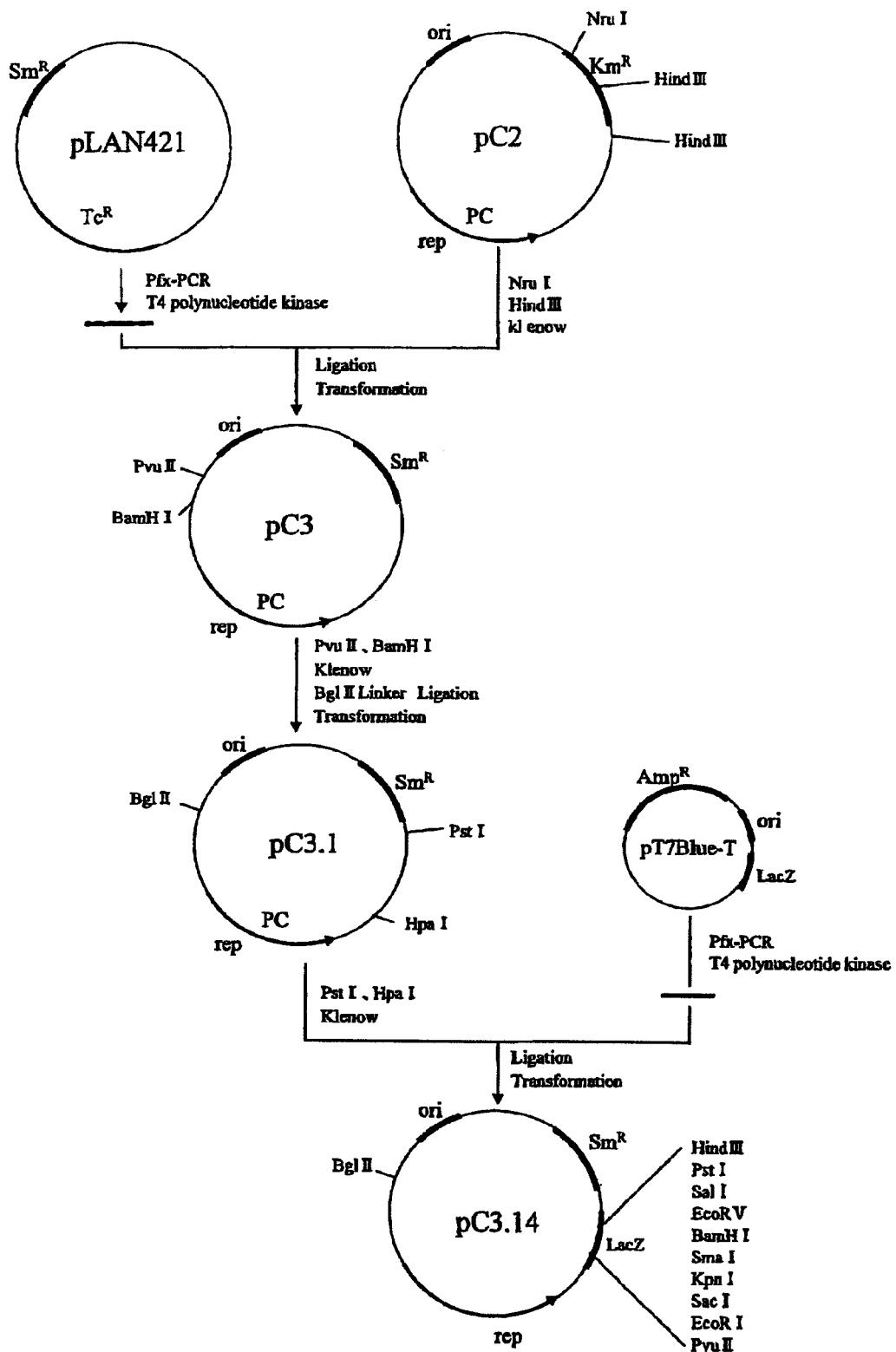
FIG. 1 is a diagram illustrating a procedure for constructing plasmid pC3.14.

Hereinafter, embodiments of the present invention will be described in detail.

The bacterium of the present invention is a bacterium having an organic acid-producing ability which is modified so that 2-oxoglutarate dehydrogenase (hereinafter, also referred to as ODH) activity is enhanced as compared with an unmodified strain.

In the present invention, the term "organic acid-producing ability" refers to an ability to accumulate an organic acid in a medium when the bacterium of the present invention is cultured in the medium. Examples of "organic acid" include organic acids serving as a metabolic intermediate in TCA cycle, and specific examples thereof include succinic acid, malic acid, fumaric acid, citric acid, isocitric acid, and cis-aconitic acid. Of these, succinic acid, malic acid, and fumaric acid are preferable, and succinic acid is more preferable.

The bacterium may be a bacterium obtained by modifying a bacterium having an organic acid-producing ability intrinsically or a bacterium that has been imparted with an organic acid-producing ability by breeding to enhance ODH activity, or may be a bacterium that becomes to have an organic acid-producing ability by the modification to enhance ODH activity. As a method of imparting the organic acid-producing ability by breeding, a mutation treatment or a gene recombination treatment can be exemplified. Specific examples thereof include a modification to decrease lactate dehydrogenase activity and a modification to enhance pyruvate carboxylase activity as described below.

The bacterium used in the present invention may be one having an ability of producing two or more kinds of the organic acids.

The bacterium that can be used in the method of the present invention is not limited as long as it has an organic acid-producing ability. A coryneform bacterium, a bacterium belonging to the genus *Bacillus*, a bacterium belonging to the genus *Escherichia*, a bacterium belonging to the genus *Lactobacillus*, a bacterium belonging to the genus *Saccinobacillus*, and a bacterium belonging to the genus *Rhizobium* are preferable. Of these, a coryneform bacterium is more preferable.

As the bacterium belonging to the genus *Escherichia*, *Escherichia coli* can be exemplified. As the bacterium belonging to the genus *Lactobacillus, Lactobacillus helveticus* can be exemplified (J Appl Microbiol, 2001, 91, p 846-852). Examples of the bacterium belonging to the genus *Bacillus* include *Bacillus subtilis, Bacillus amyloliquefaciens, Bacillus pumilus,* and *Bacillus stearothermophilus*. As the bacterium belonging to the genus *Rhizobium, Rhizobium etli* can be exemplified.

The coryneform bacterium is not particularly limited as long as it is classified into the coryneform bacterium. Examples thereof include a bacterium belonging to the genus *Corynebacterium*, a bacterium belonging to the genus *Brevibacterium*, and a bacterium belonging to the genus *Arthrobacter*. Of these, a bacterium belonging to the genus *Corynebacterium* or a bacterium belonging to the genus *Brevibacterium* is preferable. More preferable examples include bacteria classified into *Corynebacterium glutamicum, Brevibacterium flavum, Brevibacterium ammoniagenes,* and *Brevibacterium lactofermentum*.

Particularly preferable examples of parent strains of the bacteria used in the present invention include *Brevibacterium flavum* MJ-233 (FERM BP-1497), *Brevibacterium flavum* MJ-233 AB-41 (FERM BP-1498), *Brevibacterium ammoniagenes* ATCC6872, *Corynebacterium glutamicum* ATCC31831, and *Brevibacterium lactofermentum* ATCC 13869. Since *Brevibacterium flavum* is sometimes classified into *Corynebacterium glutamicum* (Lielbi, W., Ehrmann, M., Ludwig, W. and Schleifer, K. H., International Journal of Systematic Bacteriology, 1991, vol. 41, p 255-260), *Brevibacterium flavum* MJ-233 strain and its mutant, MJ-233 AB-41 strain, are identical to *Corynebacterium glutamicum* MJ-233 strain and *Corynebacterium glutamicum* MJ-233 AB-41 strain, respectively, in the present invention.

*Brevibacterium flavum* MJ-233 has been deposited with the Accession No. FERM P-3068 at National Institute of Bioscience and Human-Technology, Agency of Industrial Science and Technology, Ministry of International Trade and Industry (currently, International Patent Organism Depositary, National Institute of Advanced Industrial Science and Technology) (Central 6, 1-1-1 Higashi, Tsukuba, Ibaraki, 305-8566 Japan) on Apr. 28, 1975, followed by being transferred to an international deposit under the provisions of Budapest Treaty on May 1, 1981 with the Accession No. FERM BP-1497.

The above-mentioned bacteria used as parent strains may be any strains including not only wild-type strains, but also mutants obtained by usual mutation treatment such as UV irradiation and an NTG treatment, and recombinant strains obtained by a genetic method such as cell fusion and a genetic recombination method.

The bacteria of the present invention can be obtained by modifying the above-mentioned bacteria having an organic acid-producing ability so that ODH activity is enhanced. A modification to impart the organic acid-producing ability may be performed after modification to enhance ODH activity was carried out.

Here, the term "ODH activity" refers to the activity that catalyzes a reaction in which 2-oxoglutarate (α-ketoglutarate) is oxidatively decarboxylated to generate succinyl-CoA. The term "ODH activity is enhanced" refers to that ODH activity is enhanced as compared with an ODH-unmodified strain. The ODH activity is enhanced preferably not less than 1.5 times higher than that of the ODH-unmodified strain per unit weight of bacterial cells, and more preferably not less than twice higher than that of the ODH unmodified strain. The ODH activity can be measured according to the method of Shiio et al. (Isamu Shiio and Kyoko Ujigawa-Takeda, Agric. Biol. Chem., 44 (8), 1897-1904, 1980).

A modification to enhance ODH activity using an ODH gene can be performed, for example, by transformation using a plasmid or the like, integration of the ODH gene into a chromosome by homologous recombination or the like, or a modification of an expression control sequence of the ODH gene.

An ODH gene that can be used to introduce an ODH gene into a host bacterium by transformation using a plasmid etc., homologous recombination, or the like is not limited as long as it is a gene that increases the ODH activity when the gene is introduced into the host bacterium, that is, a gene that encodes a protein having an ODH activity. The ODH gene (odhA) derived from a coryneform bacterium and having the nucleotide sequence shown in SEQ ID NO: 3 can be exemplified. The ODH gene may be a homolog gene such as a DNA that hybridizes with a DNA having the above-mentioned nucleotide sequence under stringent conditions, or a DNA having a nucleotide sequence not less than 90% homologous, preferably not less than 95% homologous, and more preferably not less than 99% homologous to the above-mentioned nucleotide sequence as long as it encodes a protein having ODH activity.

Here, the stringent conditions include washing conditions for usual southern hybridization, and preferably include conditions under which hybridization is performed at 60° C., and at a salt concentration equivalent to 1×SSC, and 0.1% SDS, preferably 0.1×SSC and 0.1% SDS.

In addition, an ODH gene derived from bacteria other than the coryneform bacterium, other microorganisms, animals, or plants can also be used. As the ODH gene derived from microorganisms, animals, or plants, the following genes can be used: a gene of which nucleotide sequence has already been determined; and a gene of which nucleotide sequence to be determined after isolating the gene encoding a protein having an ODH activity from a chromosome of microorganisms, animals, or plants based on homology or the like. Further, after the nucleotide sequence of a gene is determined, a gene synthesized based on the nucleotide sequence can also be used. These genes can be obtained by amplifying regions including a promoter and an ORF by a hybridization method or a PCR method.

By inserting a DNA fragment comprising the above-mentioned ODH gene into a suitable plasmid such as a plasmid vector containing at least a gene controlling a replication function of a plasmid in a coryneform bacterium, a recombinant plasmid capable of expressing ODH to a high degree in the coryneform bacterium can be obtained. In the above-mentioned recombinant plasmid, a promoter for expressing the ODH gene may be a promoter originated from the ODH gene itself, but the promoter may be replaced with another strong promoter that can function in a host bacterium. A promoter derived from *E. coli*, such as a tac promoter or a trc promoter can be exemplified.

When the ODH gene is introduced into the coryneform bacterium, a plasmid vector that can be used is not limited as long as it contains at least a gene controlling a replication function in the coryneform bacterium. Specific examples of the plasmid vectors include: the plasmid pCRY30 described in JP-A-3-210184; the plasmids pCRY21, pCRY2KE, pCRY2KX, pCRY31, pCRY3KE, and pCRY3KX described in JP-A-2-72876 and U.S. Pat. No. 5,185,262; the plasmids pCRY2 and pCRY3 described in JP-A-1-191686; pAM330 described in JP-A-58-67679; pHM1519 described in JP-A-58-77895; pAJ655, pAJ611, and pAJ1844 described in JP-A-58-192900; pCG1 described in JP-A-57-134500; pCG2 described in JP-A-58-35197; pCG4 and pCG11 described in JP-A-57-183799; and pPK4 described in WO 95/34672. Of these, as a plasmid vector to be used in the host-vector system of the coryneform bacterium, a plasmid vector having a gene controlling a replication function of a plasmid in the coryneform bacterium and a gene controlling a stabilization function of a plasmid in the coryneform bacterium is preferable. For example, the plasmids pCRY30, pCRY21, pCRY2KE, pCRY2KX, pCRY31, pCRY3KE, and pCRY3KX can be preferably used.

By transforming a coryneform bacterium such as *Brevibacterium flavum* MJ-233 strain (FERM BP-1497) with a recombinant vector obtained by inserting the ODH gene into an appropriate site of a plasmid vector, a coryneform bacterium in which the expression of the ODH gene is enhanced is obtained. Transformation can be performed by a known method such as the electric pulse method (Res. Microbiol., Vol. 144, p. 181-185, 1993).

ODH activity can also be enhanced by incorporating multiple copies of the ODH gene into a chromosome by a known homologous recombination method so that the ODH gene is expressed to a high degree.

An example of using the coryneform bacterium has been described above, but the ODH activity can also be enhanced by the similar way when other bacteria are used.

Moreover, the ODH activity can also be enhanced by substituting a promoter on a chromosome of a host. Sequence information of a promoter region can be obtained from, for example, GenBank, Database Accession No. AP005276. A kind of the promoter to be substituted is not particularly limited as long as it is capable of functioning in a host bacterium. A promoter whose transcription activity is not suppressed under an anaerobic condition is preferable. Examples thereof include a tac promoter and a trc promoter which are used in *E. coli*.

As a method for promoter substitution, a method of using the sacB gene shown in the Examples described below (Schafer, A. et al. Gene 145 (1994) 69-73) can be exemplified.

In the present invention, modification to enhance ODH activity may be performed in an organic acid-producing bacterium that has been modified so that acetic acid production is decreased. In an organic acid-producing bacterium modified so that acetic acid production is decreased, 2-oxoglutarate is sometimes formed as a by-product. Since ODH catalyzes a reaction to oxidatively decarboxylate 2-oxoglutarate to generate succinyl-CoA, enhancement of the ODH activity leads to a reduction in the amount of 2-oxoglutarate as a by-product and an increase in the production of the target organic acid.

Examples of a modification so that acetic acid production is decreased include a modification to decrease respective activities of acetate kinase (hereinafter also referred to as ACK), phosphotransacetylase (hereinafter also referred to as PTA), acetyl-CoA hydrolase (hereinafter also referred to as ACH), and pyruvate oxidase (hereinafter also referred to as POXB).

Because acetic acid is generated from acetyl-CoA as an intermediate product in a biosynthetic pathway of oxaloacetate and oxaloacetate derivatives, it is preferable that any one of the activities of the above-mentioned enzymes or the activities of all the enzymes be decreased so that the amount of acetic acid as a by-product is decreased by blocking the acetic acid biosynthetic pathway.

The term "PTA activity" refers to an activity of catalyzing a reaction which generates acetyl phosphate by transferring phosphate to acetyl-CoA. The phrase "modified so that a PTA activity is decreased" means that the PTA activity is lower than a specific activity of an unmodified strain such as a wild-type strain. The PTA activity is decreased to preferably 30% or less and more preferably 10% or less per bacterial cell as compared with an unmodified strain. The PTA activity may be completely eliminated. The decrease in PTA activity can be confirmed by measurement of the PTA activity by a method of Klotzsch et al. (Klotzsch, H. R., Meth Enzymol. 12, 381-386 (1969)).

The term "ACK activity" refers to an activity of catalyzing a reaction which generates acetic acid from acetyl phosphate and ADP. The phrase "modified so that an ACK activity is decreased" means that the ACK activity is lower than a specific activity of an unmodified strain such as a wild-type strain. The ACK activity is decreased to preferably 30% or less and more preferably 10% or less per bacterial cell as compared with an unmodified strain. The ACK activity may be completely eliminated. The decrease in ACK activity can be confirmed by measurement of the ACK activity by a method of Ramponi et al. (Ramponi G., Meth. Enzymol. 42, 409-426 (1975)).

In *Corynebacterium glutamicum* (including a bacterium classified into *Brevibacterium flavum*), the both enzymes are encoded by the pta-ack operon as described in Microbiology. 1999 February; 145 (Pt 2): 503-13, so the activities of both enzymes, PTA and ACK, can be decreased by disrupting the pta gene.

Disruption of the pta gene can be conducted according to a known method such as a method using a homologous recombination or a method using the sacB gene (Schafer, A. et al. Gene 145 (1994) 69-73). As the pta gene, a DNA comprising the nucleotide sequence of nucleotide numbers 1 to 1383 shown in SEQ ID NO: 7 can be exemplified. Further, since the gene to be used for disruption of the pta gene may have homology in such a degree that is sufficient for causing homologous recombination with the pta gene on a chromosomal DNA of a coryneform bacterium as a target for disruption, a gene homologous to the sequence can also be used. Here, the homology in such a degree that is sufficient for causing homologous recombination means homology of preferably not less than 70%, more preferably not less than 80%, still more preferably not less than 90%, and particularly preferably not less than 95%. In addition, DNAs that can hybridize with the above-mentioned gene under stringent conditions may undergo homologous recombination with each other.

The modification may be performed by using the ack gene when only the ACK activity is decreased. An example of the ack gene includes a gene having the nucleotide sequence of nucleotide numbers 1386 to 2579 shown in SEQ ID NO: 7. Besides, a gene having homology to the sequence in such a degree that is sufficient for causing homologous recombination with the ack gene on a chromosome can also be used. Here, the homology in such a degree that is sufficient for causing homologous recombination means homology of preferably not less than 70%, more preferably not less than 80%, still more preferably not less than 90%, and particularly preferably not less than 95%. In addition, DNAs that can hybridize with the above-mentioned gene under stringent conditions may undergo homologous recombination with each other.

The bacterium used in the present invention may be a bacterium that is obtained by a combination of two or more kinds of the above-mentioned modification in addition to the modification to enhance the ODH activity. When multiple modifications are performed, the order of each modification is not particularly limited.

The term "ACH activity" refers to an activity of catalyzing a reaction which generates acetic acid from acetyl-CoA and water. The phrase "modified so that an ACH activity is decreased" means that the ACH activity is lower than a specific activity of an unmodified strain such as a wild-type strain. The ACH activity is decreased to 50% or less, preferably 30% or less, and more desirably 10% or less per bacterial cell as compared with an unmodified strain. The term "decreased" also includes complete elimination of the activity. The decrease in ACH activity can be confirmed by measurement of the ACH activity by the method of Gergely, J., et al. (Gergely, J., Hele, P. & Ramkrishnan, C. V. (1952) J. Biol. Chem. 198 p 323-334). Examples of the gene encoding the ACH of a coryneform bacterium include the sequence of *Corynebacterium glutamicum* (NCgl2480 in GenBank Accession No. NC_003450 (a strand complementary to the nucleotide numbers of 2729376 to 2730884 in NC_003450)) deposited in GenBank (WO 2005/113744). The sequence of the ach gene of *Corynebacterium glutamicum* is also shown in 1037 to 2545 of SEQ ID NO: 14. In addition, a gene having homology to the sequence in such a degree that is sufficient for causing homologous recombination with the ach gene in a chromosome can also be used. Here, the homology in such a degree that is sufficient for causing homologous recombination means homology of preferably not less than 70%, more preferably not less than 80%, still more preferably not less than 90%, and particularly preferably not less than 95%. In addition, DNAs that can hybridize with the above-mentioned gene under stringent conditions may undergo homologous recombination with each other.

The term "POXB activity" refers to an activity of catalyzing a reaction which generates acetic acid from pyruvic acid and water. The phrase "modified so that a POXB activity is decreased" means that the POXB activity is lower than a specific activity of an unmodified strain such as a wild-type strain. The POXB activity is decreased to preferably 50% or less, more preferably 30% or less, and particularly preferably 10% or less per bacterial cell as compared with an unmodified strain. The term "decreased" also includes complete elimination of the activity. The decrease in POXB activity can be confirmed by measurement of the POXB activity by the method of Chang et al. (Chang Y. and Cronan J. E. JR, J. Bacteriol. 151, 1279-1289 (1982)). Examples of the poxB gene of a coryneform bacterium include the sequence (a strand complementary to the nucleotide numbers of 2776766 to 2778505 in GenBank Accession No. NC_003450) deposited in GenBank (WO 2005/113745). The sequence of the poxB gene of *Corynebacterium glutamicum* is also shown in 996 to 2735 of SEQ ID NO: 16. In addition, a gene having homology to the sequence in such a degree that is sufficient for causing homologous recombination with the poxB gene on a chromosome can also be used. Here, the homology in such a degree that is sufficient for causing homologous recombination means homology of preferably not less than 70%, more preferably not less than 80%, still more preferably not less than 90%, and particularly preferably not less than 95%. In addition, DNAs that can hybridize with the above-mentioned gene under stringent conditions may undergo homologous recombination with each other.

Disruption of the ach gene and the poxB gene can be performed by a known method, in the similar way to that for the disruption of the pta gene as described above.

The bacterium of the present invention may be a bacterium modified so that a lactate dehydrogenase (hereinafter also referred to as LDH) activity is decreased in addition to the enhancement of ODH activity. Such a bacterium is particularly effective when an organic acid is succinic acid. Such a bacterium can be obtained, for example, by preparation of a LDH gene-disrupted bacterium, followed by modification of the bacterium with the ODH gene. It should be noted that either of the modification to decrease LDH activity and modification to enhance ODH activity may be performed first.

The phrase "LDH activity is decreased" means that the LDH activity is lower as compared with that of an LDH gene unmodified strain. The LDH activity is preferably decreased to 10% or less per bacterial cell as compared with that of the unmodified strain. Further, the LDH activity may be completely eliminated. The decrease in LDH activity can be confirmed by measurement of the LDH activity by a known method (L. Kanarek and R. L. Hill, J. Biol. Chem. 239, 4202 (1964)). As a specific method for obtaining a strain of a coryneform bacterium whose LDH activity is decreased, the method using homologous recombination on a chromosome described in JP-A-11-206385, the method using the sacB gene (Schafer, A. et al. Gene 145 (1994) 69-73), and the like can be exemplified.

In addition, the bacterium used in the present invention may be a bacterium modified so that pyruvate carboxylase (hereinafter also referred to as PC) activity is enhanced in addition to the enhancement in ODH activity. The phrase "PC activity is enhanced" means that the PC activity is increased preferably 100% or more, and more preferably 300% or more as compared with that of unmodified strains such as a wild-type strain and a parent strain. The PC activity can be measured, for example, by a method of measuring a decrease in NADH (WO 2005/021770). Such a bacterium can be obtained, for example, by introducing the PC gene into a coryneform bacterium in which the expression of the ODH gene is enhanced. It should be noted that either of the introduction of the PC gene and the modification to enhance the ODH activity may be performed first.

The introduction of the PC gene can be performed by expressing the pyruvate carboxylase (PC) gene in a coryneform bacterium to a high degree in the similar manner to that described in JP-A-11-196888. As a PC gene, for example, a PC gene derived from *Corynebacterium glutamicum* (Peters-Wendisch, P. G. et al. Microbiology, vol. 144 (1998) p 915-927 (SEQ ID NO: 5)) can be used. In the nucleotide sequence of SEQ ID NO: 5, a part of the nucleotides may be replaced with other nucleotides, or may be deleted, new nucleotides may be inserted, or a part of the nucleotides may be translocated as long as the PC activity is not substantially impaired. Any of these derivatives can be used in the present invention. Further, the following DNAs can also be suitably used: a DNA that hybridizes with a DNA comprising the nucleotide sequence of SEQ ID NO: 5 under stringent conditions; a DNA which has homology of not less than 90%, preferably not less than 95%, and more preferably not less than 99% to the nucleotide sequence of SEQ ID NO: 5 and encodes a protein having a PC activity.

In addition, a PC gene derived from bacteria other than *Corynebacterium glutamicum*, other bacteria, animals, or plants can also be used. In particular, the sequences of the PC genes derived from the following bacteria, animals, and plants are already known (the reference documents are shown below), or the PC genes can be obtained by hybridization in the similar manner as described above or by amplifying the ORF by a PCR method.

Human [Biochem. Biophys. Res. Comm., 202, 1009-1014, (1994)]
Mouse [Proc. Natl. Acad. Sci. USA., 90, 1766-1779, (1993)]
Rat [GENE, 165, 331-332, (1995)]
Yeast; *Saccharomyces cerevisiae* [Mol. Gen. Genet., 229, 307-315, (1991)]*Schizosaccharomyces pombe* [DDBJ Accession No.; D78170]
*Bacillus stearothermophilus* [GENE, 191, 47-50, (1997)]
*Rhizobium etli* [J. Bacteriol., 178, 5960-5970, (1996)]

The enhancement of the PC activity can be performed in the similar manner to the enhancement of the ODH activity as described above.

2. Production Method of Organic Acid

The method for producing an organic acid of the present invention comprises allowing the above-mentioned bacteria or treated cell thereof to act on an organic raw material in a reaction solution containing a carbonate ion, a bicarbonate ion, or carbon dioxide gas to produce an organic acid, and collecting the organic acid. The organic acids to be produced include the above-mentioned organic acids. Of these, succinic acid, fumaric acid, malic acid, or pyruvic acid is preferable, and succinic is more preferable.

When the above-mentioned bacteria is used in the production of an organic acid, those subjected to slant culture on a solid medium such as an agar medium may be used directly for the reaction, but bacterial cells prepared by culturing the above-mentioned bacteria in a liquid medium (i.e., seed culture) in advance may preferably be used. The medium to be used for the seed culture may be any of those normally used for the culture of bacteria. For example, a common medium, which is prepared by adding natural nutrient sources such as meat extract, yeast extract, and peptone to a composition formed of inorganic salts such as ammonium sulfate, potassium phosphate, and magnesium sulfate, can be used. The bacterial cells after the seed culture are preferably used for production reaction of an organic acid after being harvested by centrifugation, membrane separation, or the like. The organic acid may be produced by allowing the bacterium obtained by the seed culture to react with an organic raw material in a medium containing the organic raw material while proliferating the bacterium. Alternatively, the organic acid may be produced by allowing the bacterial cells obtained by being proliferated in advance to react with the organic raw material in a reaction solution containing the organic raw material.

In the present invention, treated bacterial cells can also be used. Examples of the treated bacterial cells include bacterial cells immobilized with acrylamide, carrageenan, or the like, debris of crushed bacterial cells, a centrifuged supernatant thereof, or fractions obtained by partially purifying the supernatant with an ammonium sulfate treatment or the like.

An organic raw material to be used for the production method of the present invention is not particularly limited as long as it is a carbon source which can be assimilated by the bacteria described herein to generate an organic acid such as succinic acid. In general, there is used a fermentable carbohydrate including: a carbohydrate such as galactose, lactose, glucose, fructose, glycerol, sucrose, saccharose, starch, or cellulose; or polyalcohols such as glycerin, mannitol, xylitol, or ribitol. Of these, glucose or sucrose is preferable, and glucose is particularly preferable.

In addition, a starch saccharification liquid, molasses, or the like, which contains any one of the above-mentioned fermentable carbohydrates, can also be used. Any one of these fermentable carbohydrates may be used alone or may be used in combination. The concentration at which the above-mentioned organic raw material is used is not specifically limited, but it is advantageous to increase the concentration as much as possible within the range that does not inhibit the generation of an organic acid such as succinic acid. A reaction is generally performed in the range of 5 to 30% (W/V), and preferably 10 to 20% (W/V). The above-mentioned organic raw material may be further added when the organic raw material is decreased in the course of the reaction.

The reaction solution containing the organic raw materials is not specifically limited. The reaction solution to be used may be a medium for culturing bacteria or a buffer such as a phosphate buffer. The reaction solution is preferably an aqueous solution containing a nitrogen source, inorganic salts, and the like. Here, the nitrogen source is not specifically limited as long as it can be assimilated by the bacteria described herein to generate an organic acid such as succinic acid. Specific examples thereof include various organic and inorganic nitrogen compounds such as ammonium salts, nitrate, urea, a soybean hydrolysate, a casein catabolite, peptone, yeast extract, meat extract, and corn steep liquor. Examples of the inorganic salts include various kinds of phosphates, sulfates, and metal salts of magnesium, potassium, manganese, iron, zinc, and the like. In addition, any factors that promote the growth, including: vitamins such as biotin, pantothenic acid, inositol, and nicotinic acid; nucleotides; and amino acids, may be added if necessary. Further, it is desirable that an appropriate amount of a commercially available antifoaming agent be added to the culture solution to suppress foaming at the time of reaction.

The reaction solution contains carbonate ions, bicarbonate ions, or carbon dioxide gas in addition to the above-mentioned organic raw materials, nitrogen source, inorganic salts, and the like. The carbonate ions or the bicarbonate ions may be supplied from magnesium carbonate, sodium carbonate, sodium bicarbonate, potassium carbonate, or potassium bicarbonate, which can also be used as a neutralizing agent. However, if required, the carbonate ions or the bicarbonate ions can also be supplied from carbonate or bicarbonate, or salts thereof, or carbon dioxide gas. Specific examples of the salts of carbonate or bicarbonate include magnesium carbonate, ammonium carbonate, sodium carbonate, potassium carbonate, ammonium bicarbonate, sodium bicarbonate, and potassium bicarbonate. The carbonate ions or bicarbonate ions are added at a concentration of 1 to 500 mM, preferably 2 to 300 mM, and more preferably 3 to 200 mM. When carbon dioxide gas is to be contained, the amount of the carbon dioxide gas to be contained is 50 mg to 25 g, preferably 100 mg to 15 g, and more preferably 150 mg to 10 g per liter of the solution.

The pH of the reaction solution can be adjusted by addition of sodium carbonate, sodium bicarbonate, potassium carbonate, potassium bicarbonate, magnesium carbonate, sodium hydroxide, calcium hydroxide, magnesium hydroxide, or the like. The pH for the reaction is usually 5 to 10, preferably 6 to 9.5, so the pH of the reaction solution is adjusted, if required, within the above-mentioned range with an alkaline material, carbonate, urea, or the like even during the reaction.

The optimal temperature at which the bacteria to be used in the reaction grow is generally in the range of 25° C. to 35° C. The temperature at the time of the reaction is generally in the range of 25° C. to 40° C., and preferably in the range of 30° C. to 37° C. The amount of bacterial cells to be used in the reaction is not specifically limited, but the amount is adjusted in the range of 1 to 700 g/L, preferably 10 to 500 g/L, and more preferably 20 to 400 g/L. The time period of the reaction is preferably 1 to 168 hours, and more preferably 3 to 72 hours.

When seed culture of bacteria is performed, there is a need of supplying oxygen by aeration and agitation. On the other hand, a reaction for producing an organic acid such as succinic acid may be performed with aeration and agitation, or may be performed under anaerobic conditions with neither aeration nor supply of oxygen. Here, the term "anaerobic condition" means that a reaction is conducted while the dissolved oxygen level is kept low in a solution. In this case, it is desirable to carry out the reaction at dissolved oxygen levels of 0 to 2 ppm, preferably 0 to 1 ppm, and more preferably 0 to 0.5 ppm. For that purpose, there may be used methods including: carrying out the reaction with a vessel hermetically sealed without aeration; carrying out the reaction while supplying an inert gas such as nitrogen gas; and performing aeration with an inert gas containing carbon dioxide gas.

The above-mentioned bacterial reaction leads to generation and accumulation of organic acids such as succinic acid, fumaric acid, malic acid, or pyruvic acid in a reaction solution. The organic acids accumulated in the reaction solution (culture solution) can be collected from the reaction solution according to the conventional procedures. Specifically, the organic acids can be collected by removing a solid substance such as bacterial cells through centrifugation, filtration, or the like, and desalting the remainings with an ion exchange resin or the like, followed by crystallization or purification by column chromatography from the solution.

Further, in the present invention, after the production of the organic acids by the method of the present invention described above, a polymerization reaction may be carried out using the obtained organic acids as a raw material to produce organic acid-containing polymers.

In recent years, while the number of environment-friendly industrial products is on the increase, polymers prepared by using raw materials of a plant origin have been attracting attention. The succinic acid to be produced in the present invention can be processed into polymers such as polyester and polyamide and then used. Specific examples of a succinic acid-containing polymer include succinic acid polyesters obtained through polymerization between a diol such as butanediol or ethylene glycol and succinic acid, and succinic acid polyamides obtained through polymerization between a diamine such as hexamethylenediamine and succinic acid.

In addition, the succinic acid obtained by the production method of the present invention or a composition containing the succinic acid can be used for food additives, pharmaceuticals, cosmetics, and the like.

EXAMPLE 1

<Preparation of ODH-plasmid Amplified Strain>

(A) Extraction of Genomic DNA from MJ233 Strain

In 10 mL of A medium [2 g of urea, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 6 mg of $MnSO_4.4-5H_2O$, 200 μg of biotin, 100 μg of thiamine, 1 g of yeast extract, 1 g of casamino acid, and 20 g of glucose were dissolved in 1 L of distilled water], *Brevibacterium flavum* MJ-233 strain was cultured until the late stage of logarithmic phase, and bacterial cells were collected by centrifugation (10,000 g, 5 minutes). The obtained bacterial cells were suspended in 0.15 mL of a solution containing 10 mg/mL of lysozyme, 10 mM NaCl, 20 mM Tris buffer (pH of 8.0), and 1 mM EDTA•2Na. Next, proteinase K was added thereto so as to be a final concentration of 100 μg/mL, and the resultant was kept at 37° C. for 1 hour. Sodium dodecyl sulfate was further added so as to be a final concentration of 0.5%, and the resultant was kept at 50° C. for 6 hours for bacteriolysis. To the lysate, a solution of an equivalent amount of phenol and chloroform was added, and the mixture was slowly shaken at room temperature for 10 minutes. Subsequently, the whole was centrifuged (5,000×g for 20 minutes at 10 to 12° C.), and the supernatant fraction was collected. Sodium acetate was added thereto so as to be 0.3 M, and 2 equivalents of ethanol were added and mixed. The mixture was subjected to centrifugation (15,000×g for 2 minutes) to collect the precipitate. The collected precipitate was washed with 70% ethanol and then dried by blowing air. To the obtained DNA, 5 mL of a solution of 10 mM Tris buffer (pH of 7.5) containing 1 mM EDTA·2Na were added, and left to stand at 4° C. overnight. The obtained DNA was used as a template DNA for PCR carried out later.

(B) Cloning of ODH Gene and Construction of a Plasmid for Enhancement

The gene (odhA) including a promoter region of 2-oxoglutarate dehydrogenase complex E1 component derived from *Brevibacterium flavum* MJ-233 strain was obtained by performing PCR by using the DNA prepared in the above (A) as a template, and synthesized DNAs (SEQ ID NO: 1 and SEQ ID NO: 2), which were designed based on the sequence of the gene (a strand complementary to 1172498 to 1176271 of GenBank Database Accession No. BA000036) of *Corynebacterium glutamicum* ATCC13032 strain, whose entire genomic sequence has been reported. A reaction solution was composed of 1 µL of the template DNA, 0.5 µL of PfxDNA polymerase (manufactured by Invitrogen Corporation), the attached buffer at 1-fold concentration, 0.4 µL each of the primers, 1 mM MgSO$_4$, and 0.2 g MdNTPs, and the total volume was adjusted to 50 µL. Reaction temperature and reaction conditions were as follows: the DNA thermal cycler PTC-200 (manufactured by MJ Research Inc.) was used; and a cycle of 94° C. for 10 seconds and 68° C. for 5 minutes was repeated 35 times, provided that the reaction solution was kept at 94° C. for 2 minutes in the first cycle and was kept at 68° C. for 10 minutes in the final cycle. After completion of the PCR reaction, 0.1 µL of Takara Ex Taq (TAKARA BIO INC.) was added, and the mixture was further kept at 72° C. for 30 minutes. The amplified product was confirmed as follows: the amplified product was separated by being subjected to 0.75% agarose (SeaKem GTG agarose: manufactured by FMC Bioproducts Inc.) gel electrophoresis; then visualized by being subjected to ethidium bromide dye staining; and thereby a fragment of about 4.4 kb was detected. The target DNA fragment was collected from the gel by using QIAQuick Gel Extraction Kit (manufactured by QIAGEN GmbH). The collected DNA fragment was mixed with a PCR product-cloning vector, pT7Blue T-Vector (manufactured by Novagen Inc.), and the both were ligated with each other by using Ligation Kit ver. 2 (TAKARA BIO INC.). The obtained plasmid DNA was used to transform *E. coli* (DH5α strain). The thus obtained recombinant *E. coli* was spread on an LB agar medium containing 50 µg/mL ampicillin and 50 µg/mL X-Gal. The clone that formed a white colony on the medium was cultured in a liquid medium by a conventional method, followed by purification of plasmid DNA. The obtained plasmid DNA was cleaved with the restriction enzymes SseI and BamHI, thereby an inserted fragment of about 4.4 kb was detected. The obtained plasmid DNA was named pODH1.0.

(C) Construction of Expression Vector for Coryneform Bacterium Having Compatibility with pTZ4

(i) Introduction of Streptomycin/Spectinomycin-resistant Gene

A vector for coryneform bacterium that is capable of coexisting with pTZ4 was constructed by replacing the kanamycin-resistant gene of the plasmid vector pC2 (Plasmid 36 62 (1996)) having a replication region compatible with pTZ4 with the streptomycin/spectinomycin-resistant gene. It should be noted that pTZ4 is the original plasmid of a plasmid for PC amplification introduced into the MJ233/PC/ΔLDH strain described below.

The streptomycin/spectinomycin-resistant gene (*E. coli* Tn7) was obtained by PCR in which the binary vector pLAN421 (Plant Cell Reports 10, 286 (1991)) for plant transformation carrying the gene was used as a template.

A reaction solution was composed of 10 ng of the template DNA, 0.2 µL of PfxDNA polymerase (manufactured by Invitrogen Corporation), the attached buffer at 1-fold concentration, 0.3 µL each of primers (synthesized DNAs shown in SEQ ID NO: 10 and SEQ ID NO: 11), 1 mM MgSO$_4$, and 0.25µ MdNTPs, and the total volume was adjusted to 20 µL.

Reaction temperature and reaction conditions were as follows: the DNA thermal cycler PTC-200 (manufactured by MJ Research Inc.) was used; and a cycle of 94° C. for 20 seconds, 60° C. for 20 seconds, and 72° C. for 60 seconds was repeated 20 times, provided that the reaction solution was kept at 94° C. for 1 minute and 20 seconds in the first cycle and was kept at 72° C. for 2 minutes in the final cycle.

The amplified product was confirmed as follows: the amplified product was separated by being subjected to 0.8% agarose (SeaKem GTG agarose: manufactured by FMC Bioproducts Inc.) gel electrophoresis; the product was visualized by being subjected to ethidium bromide dye staining; and a fragment of 937 bp was detected. The target DNA fragment was collected from the gel by using QIAQuick Gel Extraction Kit (manufactured by QIAGEN GmbH). The collected DNA fragment underwent phosphorylation at the 5' terminal with T4 Polynucleotide Kinase (TAKARA BIO INC.).

After pC2 was cleaved with the restriction enzymes HindIII and NruI, both ends thereof were blunted with Klenow Fragment (TAKARA BIO INC.). The DNA fragment was mixed with the streptomycin/spectinomycin-resistant genes prepared as described above, and the fragment and the gene were ligated with each other by using Ligation Kit ver. 2 (TAKARA BIO INC.). The obtained plasmid DNA was used to transform *E. coli* (DH5α strain), and 50 µg/mL spectinomycin was spread on an LB agar medium. The obtained colony was cultured in a liquid medium, and plasmid DNA was prepared by a conventional method. As a result of analysis of the above-mentioned PCR in which the synthesized DNAs of SEQ ID NO: 10 and SEQ ID NO: 11 were used as primers, insertion of the streptomycin/spectinomycin-resistant gene was confirmed. The obtained plasmid DNA was named pC3.

Next, a DNA fragment was prepared by cleaving pC3 with the restriction enzymes BamHI and PvuII, and both ends of the DNA fragment were blunted with Klenow Fragment. The DNA fragment was mixed with pBglII Linker (TAKARA BIO INC.: CAGATCTG) to perform ligation by using Ligation Kit ver. 2 (TAKARA BIO INC.). The obtained plasmid DNA was used to transform *E. coli* (DH5α strain), and the transformed *E. coli* was spread on an LB agar medium containing 50 µg/mL spectinomycin. The obtained colony was cultured in a liquid medium, and plasmid DNA was prepared by a conventional method. A plasmid DNA that could be cleaved with the restriction enzyme BglII was selected, and named pC3.1.

(ii) Introduction of a Multicloning Site

The α-peptide gene including LacZ multicloning site was prepared by PCR using *E. coli* plasmid, pT7Blue (Novagen Inc.), as a template and synthesized DNAs shown in SEQ ID NO: 12 and SEQ ID NO: 13 as primers.

A reaction solution was composed of 10 ng of template DNA, 0.2 µL of PfxDNA polymerase (manufactured by Invitrogen Corporation), the attached buffer at 1-fold concentration, 0.3 µM each of primers, 1 mM MgSO$_4$, and 0.25 µM dNTPs, and the total volume was adjusted to 20 µL.

Reaction temperature and reaction conditions were as follows: the DNA thermal cycler PTC-200 (manufactured by MJ Research Inc.) was used; and a cycle of 94° C. for 20 seconds, 60° C. for 20 seconds, and 72° C. for 30 seconds was repeated 20 times, provided that the reaction solution was kept at 94° C. for 1 minute and 20 seconds in the first cycle and was kept at 72° C. for 2 minutes in the final cycle.

The amplified product was confirmed as follows: the amplified product was separated by being subjected to 1.0% agarose (SeaKem GTG agarose: manufactured by FMC Bioproducts Inc.) gel electrophoresis; the product was visualized by being subjected to ethidium bromide dye staining; and a fragment of 577 bp was detected. The target DNA fragment was collected from the gel by using QIAQuick Gel Extraction Kit (manufactured by QIAGEN GmbH). The collected DNA fragment underwent phosphorylation at the 5' terminal with T4 Polynucleotide Kinase (TAKARA BIO INC.).

After pC3.1 was cleaved with the restriction enzymes PstI and HpaI, both ends of the DNA fragment were blunted with Klenow Fragment (TAKARA BIO INC.). The DNA fragment was mixed with the α-peptide gene fragment prepared as described above, followed by ligation by using Ligation Kit ver. 2 (TAKARA BIO INC.). The obtained plasmid DNA was used to transform *E. coli* (DH5α strain), and the transformed *E. coli* was spread on an LB agar medium containing 50 μg/mL X-Gal and 50 μg/mL spectinomycin. Blue colonies were selected from the obtained colonies. The colonies were cultured in a liquid medium, and plasmid DNAs were then prepared by a conventional method. Each of the plasmid DNAs was confirmed to have a cleavage site cleaved by EcoRV, the site being derived from the inserted LacZ multicloning site. The obtained plasmid DNA was named pC3.14 (construction procedure is shown in FIG. 1).

Figure 2:
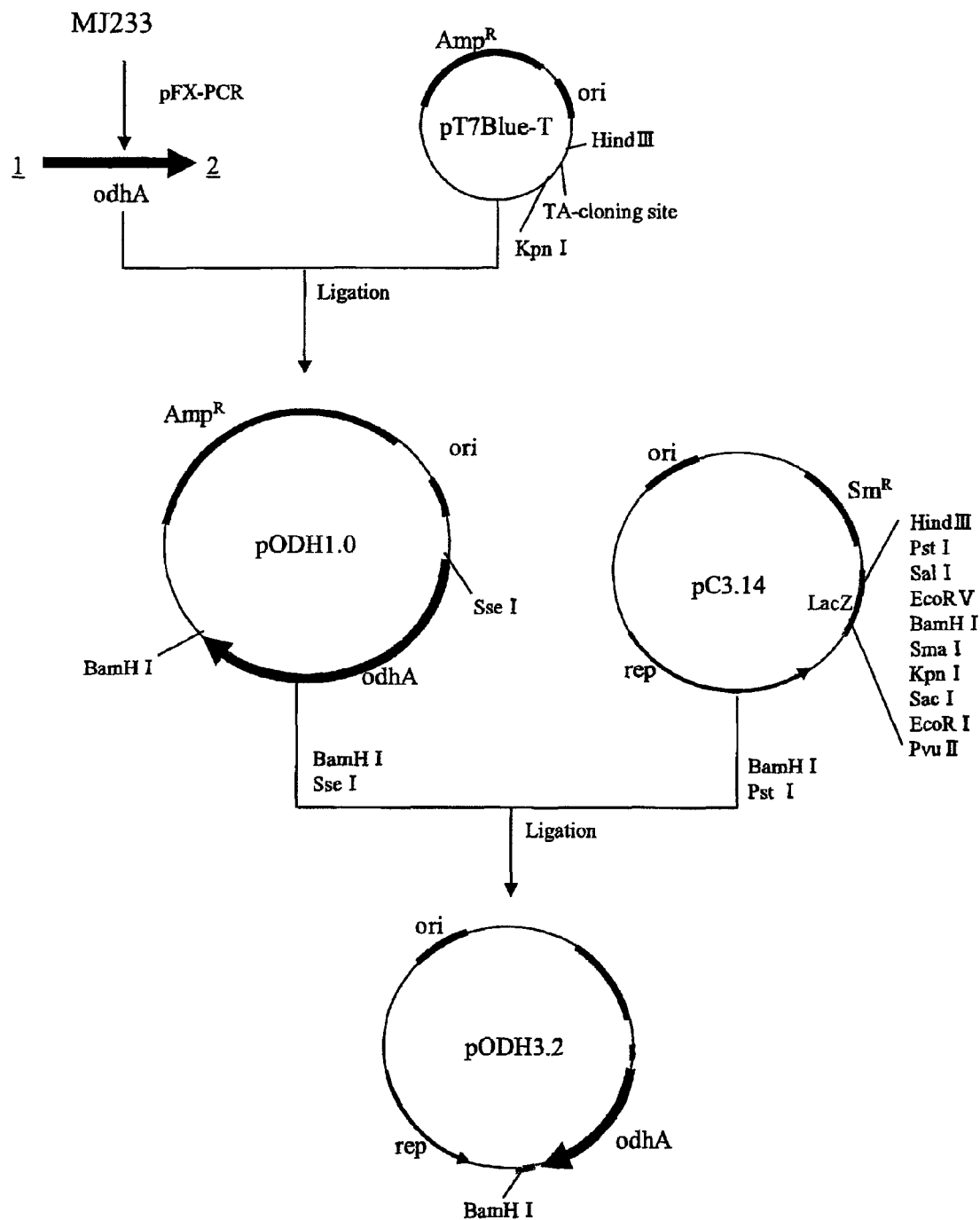
FIG. 2 is a diagram illustrating a procedure for constructing plasmid pODH3.2.

Next, a DNA fragment of about 4.4 kb obtained by cleaving the above pODH1.0 with the restriction enzymes SseI and BamHI was separated by 0.75% agarose gel electrophoresis, and collected. The obtained fragment was mixed with a DNA fragment prepared by cleaving the plasmid pC3.14 with the restriction enzymes PstI and BamHI, followed by ligation using Ligation Kit ver. 2 (TAKARA BIO INC.). The obtained plasmid DNA was used to transform *E. coli* DH5α strain. The transformed *E. coli* was spread on an LB agar medium containing 50 g/mL spectinomycin and 50 μg/mL X-Gal. A white colony that grew on the medium was cultured in a liquid medium by a conventional method, followed by purification of a plasmid DNA. The obtained plasmid DNA was cleaved with the restriction enzymes SseI and BamHI, thereby a plasmid containing an inserted fragment of about 4.4 kb was selected and named pODH3.2 (FIG. 2).

(D) Preparation of ODH Plasmid-amplified Strain

A plasmid DNA (pODH3.2) for ODH enhancement was introduced into *Brevibacterium flavum* MJ233/PC/ΔLDH strain (a strain in which the PC gene was amplified and the LDH gene was disrupted: JP-A-2005-95169: WO 2005/21770) by the electric pulse method (Res. Microbiol., Vol. 144, p. 181-185, 1993). The obtained transformant was spread on an LBG agar medium [10 g of tryptone, 5 g of yeast extract, 5 g of NaCl, 20 g of glucose, and 15 g of agar were dissolved in 1 L of distilled water] containing 10 μg/mL streptomycin and 25 μg/mL kanamycin. Each of the strains that grew on the medium was cultured in a liquid medium by a conventional method. Then, plasmid DNAs were extracted, and analyzed by cleaving with restriction enzymes. As a result, the strain was confirmed to carry pODH3.2, and named *Brevibacterium flavum* MJ233/pODH/PC/ΔLDH strain.

(E) Measurement of ODH Enzymatic Activity

The above-mentioned *Brevibacterium flavum* MJ233/pODH/PC/ΔLDH strain was cultured overnight in 100 ml of A medium containing 2% of glucose. 50 ml of the obtained culture was subjected to centrifugation at 4,000 rpm at 4° C. for 10 minutes to collect cells. After that, the strain was washed twice with 30 ml of 100 mM TES-NaOH buffer (pH of 7.5). The washed bacterial cells were suspended in 10 ml of Buffer A (100 mM TES-NaOH buffer (pH of 7.5), 30% glycerol), and 1 ml of the bacterial cell suspension was transferred to 15 ml Falcon for lysis, and 1 mg of glass beads was added thereto. The bacterial cell suspension was subjected to ultrasonic lysis (a cycle of 1 minute of sonication at High Level followed by 2 minutes of break was repeated 7 times) with Bioruptor (manufactured by Cosmo Bio Co., Ltd.) in the condition of cooling at 4° C. The bacterial cell lysis solution was subjected to centrifugation at 4° C. at 18,000×g for 5 minutes to remove beads, and was further subjected to centrifugation at 18,000×g for 25 minutes. The obtained supernatant was used as a crude enzyme fraction to measure the ODH enzymatic activity. The protein concentration was measured with Protein Assay (Bio-Rad Laboratories, Inc., #500-0006) using a BSA concentration as a standard.

ODH activity was measured as follows with reference to the method described in Agric. Boil. Chem., 44(8), 1897-1904, 1980, I Shiio and K Ujigawa-Takeda. First, an reaction solution was prepared so as to comprise the followings at final concentration: 100 mM TES (DOJINDO LABORATORIES, #344-02653)-NaOH buffer (pH of 7.7), 0.2 mM coenzyme A (Wako Pure Chemical Industries, Ltd., #306-50481), 0.3 mM thiamin pyrophosphate (Sigma-Aldrich Corporation, #C-8754), 5 mM 2-oxogulutarate (Sigma-Aldrich Corporation, #305-72-6), 3 mM L-cysteine (Wako Pure Chemical Industries, Ltd., #033-05272), 5 mM $MgCl_2$, 1 mM 3-acetylpyridine adenine dinucleotide (Wako Pure Chemical Industries, Ltd., #440-47000). After the reaction solution was transferred to a cuvette for measurement, the crude enzyme solution was added to start a reaction. Elevation of absorbance ($A_{365}$) was measured at 365 nm. 1 U was defined as an amount of enzyme when $A_{365}$ increased by 1 per minute. An ODH specific activity of *Brevibacterium flavum* MJ233/pODH/PC/ΔLDH strain measured by the above-mentioned method was 0.028 U/mg-protein. On the other hand, the bacterial cells obtained by culturing *Brevibacterium flavum* MJ233/PC/ΔLDH strain as the parent strain in the similar manner showed an ODH specific activity of 0.009 U/mg-protein. As a result, it was confirmed that an ODH activity increased by about three times in the ODH gene plasmid-amplified strain.

EXAMPLE 2

<Evaluation for the ODH-plasmid Amplified Strain>
(A) Anaerobic Fermentation Neutralized with Ammonium Carbonate To a 500-mL conical flask, 100 mL of a medium obtained by dissolving 4 g of urea, 14 g of ammonium sulfate, 0.5 g of monopotassium phosphate, 0.5 g of dibasic potassium phosphate, 0.5 g of magnesium sulfate heptahydrate, 20 mg of ferrous sulfate heptahydrate, 20 mg of manganese sulfate hydrate, 200 μg of D-biotin, 200 μg of thiamine hydrochloride, 5 g of yeast extract, and 5 g of casamino acid in 1,000 mL of distilled water was fed, which was then heated at 120° C. for 20 minutes for sterilization and then cooled to room temperature. 4 mL of 50% glucose aqueous solution preliminarily sterilized, 50 μL of 5% kanamycin aqueous solution aseptically filtered, and 50 μL of 2% streptomycin aqueous solution aseptically filtered were added thereto. Then, *Brevibacterium flavum* MJ233/ODH/PC/ΔLDH strain prepared in (D) of Example 1 was inoculated thereto for seed culture at 30° C. for 24 hours.

To a 5-L fermenter, a medium obtained by dissolving 42 g of ammonium sulfate, 1.5 g of monopotassium phosphate, 1.5 g of dibasic potassium phosphate, 1.5 g of magnesium sulfate heptahydrate, 60 mg of ferrous sulfate heptahydrate, 60 mg of manganese sulfate hydrate, 600 μg of D-biotin, 600 μg of thiamine hydrochloride, 15 g of yeast extract, 15 g of casamino acid, and 1 mL of a defoamer (Adekanol LG294: manufactured by Asahi Denka Co., Ltd.) in 2,500 mL of distilled water was fed, which was then heated at 120° C. for 20 minutes for sterilization and then cooled to room temperature. 500 mL of 12% glucose aqueous solution preliminarily sterilized, 1.5 mL of 5% kanamycin aqueous solution aseptically filtered, and 1.5 mL of 2% streptomycin aqueous solution aseptically filtered were added thereto. 100 mL of the above-mentioned seed culture was added thereto, and kept at 30° C., followed by main culture for 16 hours at pH of 7.5 maintained by using 2 M ammonium carbonate, with aeration of 500 mL per minute, and stirring at 500 rpm.

To a 500-mL conical flask, a medium obtained by dissolving 0.2 g of magnesium sulfate heptahydrate, 8 mg of ferrous sulfate heptahydrate, 8 mg of manganese sulfate hydrate, 80 μg of D-biotin, 80 μg of thiamine hydrochloride, and 1 mL of a defoamer (Adekanol LG294: manufactured by Asahi Denka Co., Ltd.) in 200 mL of distilled water was fed, which was then heated at 120° C. for 20 minutes for sterilization and then cooled to room temperature. The medium was added to the cells obtained by centrifuging the above-mentioned main culture at 8,000 rpm for 5 minutes, and the cells were suspended again so that O. D. (660 nm) became 60. 200 mL of the suspension and 200 mL of 20% glucose solution preliminarily sterilized were loaded into a 1-L jar fermenter, and mixed with each other, and the resultant was kept at 35° C. The mixture was subjected to a reaction at pH of 7.6 maintained with 2 M ammonium carbonate, under the condition of no aeration and stirring at 400 rpm. The reaction was terminated about 47 hours after the start of the reaction.

As a result, in *Brevibacterium flavum* MJ233/pODH/PC/ΔLDH strain, the yield of succinic acid increased by 3.4%, and the production amount of amino acid per succinic acid decreased by 47%, as compared with MJ233/PC/ΔLDH strain. That is, it was found that enhancement of ODH led to significant effects of improvement in the yield of succinic acid and reduction in the yield of amino acid.

(B) Anaerobic Fermentation Neutralized with Sodium Carbonate

To a 500-mL conical flask, 100 mL of a medium obtained by dissolving 4 g of urea, 14 g of ammonium sulfate, 0.5 g of monopotassium phosphate, 0.5 g of dibasic potassium phosphate, 0.5 g of magnesium sulfate heptahydrate, 20 mg of ferrous sulfate heptahydrate, 20 mg of manganese sulfate hydrate, 200 μg of D-biotin, 200 μg of thiamine hydrochloride, 5 g of yeast extract, and 5 g of casamino acid in 1,000 mL of distilled water was fed, which was then heated at 120° C. for 20 minutes for sterilization and then cooled to room temperature. 4 mL of 50% glucose aqueous solution preliminarily sterilized, 50 μL of 5% kanamycin aqueous solution aseptically filtered, and 50 μL of 2% streptomycin aqueous solution aseptically filtered were added thereto. Then, *Brevibacterium flavum* MJ233/pODH/PC/ΔLDH strain prepared in (D) of Example 1 was inoculated thereto for seed culture at 30° C. for 24 hours.

To a 5-L fermenter, a medium obtained by dissolving 42 g of ammonium sulfate, 1.5 g of monopotassium phosphate, 1.5 g of dibasic potassium phosphate, 1.5 g of magnesium sulfate heptahydrate, 60 mg of ferrous sulfate heptahydrate, 60 mg of manganese sulfate hydrate, 600 μg of D-biotin, 600 μg of thiamine hydrochloride, 15 g of yeast extract, 15 g of casamino acid, and 1 mL of a defoamer (Adekanol LG294: manufactured by Asahi Denka Co., Ltd.) in 2,500 mL of distilled water was fed, which was then heated at 120° C. for 20 minutes for sterilization and then cooled to room temperature. 500 mL of 12% glucose aqueous solution preliminarily sterilized, 1.5 mL of 5% kanamycin aqueous solution aseptically filtered, and 1.5 mL of 2% streptomycin aqueous solution aseptically filtered were added thereto. Then, 100 mL of the above-mentioned seed culture medium was added thereto, and the resultant was kept at 30° C., followed by main culture for 16 hours at pH of 7.5 maintained by using 2 M ammonium carbonate, with aeration of 500 mL per minute, and stirring at 500 rpm.

To a 500-mL conical flask, a medium obtained by dissolving 0.2 g of magnesium sulfate heptahydrate, 8 mg of ferrous sulfate heptahydrate, 8 mg of manganese sulfate hydrate, 80 μg of D-biotin, 80 μg of thiamine hydrochloride, and 1 mL of a defoamer (Adekanol LG294: manufactured by Asahi Denka Co., Ltd.) in 200 mL of distilled water was fed, which was then heated at 120° C. for 20 minutes for sterilization and then cooled to room temperature. The medium was added to the bacterial cells collected by centrifuging the culture obtained by the above-mentioned main culture at 8,000 rpm for 5 minutes, and the cells were suspended again so that O. D. (660 nm) became 60. 200 mL of the suspension and 200 mL of 20% glucose solution preliminarily sterilized were loaded into a 1-L jar fermenter, and mixed, and the resultant was kept at 35° C. The reaction was performed at pH of 7.6 maintained by using 2 M sodium carbonate, under the condition of no aeration, and stirring at 400 rpm. The reaction was terminated about 47 hours after the start of the reaction.

As a result, in *Brevibacterium flavum* MJ233/pODH/PC/ΔLDH strain, the yield of succinic acid increased by 3.8%, and the production amount of acetic acid per succinic acid decreased by 27%, as compared with MJ233/PC/ΔLDH strain. That is, it was found that enhancement of ODH led to significant effects of improvement in the yield of succinic acid and reduction in the yield of acetic acid.

EXAMPLE 3

<The Effect of ODH Enhancement in a Strain in which Acetic Acid Production was Decreased>

(A) Preparation of an ODH-Amplified Strain

An effect of enhanced 2-oxoglutarate dehydrogenase in a strain in which acetic acid production was decreased was evaluated. As the strain in which acetic acid production was decreased, a 2256 Δ (ldh, pta, ack, ach, poxB) strain was used, the strain being obtained by decreasing each of the activities of lactate dehydrogenase (ldh), acetyl-CoA hydrolase (ach), phosphotransacetylase (pta), acetate kinase (ack), and pyruvate oxidase (poxB) in *Brevibacterium lactofermentum* 2256 (*Corynebacterium glutamicum* ATCC13869) (WO 2005/113744 and WO 2005/113745).

As a plasmid for ODH amplification, pPKS-X (WO 95/34672) containing the ODH gene was used, and, pPK4 (WO 95/34672), which is the corresponding vector, was used as a control. *Brevibacterium lactofermentum* 2256 Δ (ldh, pta, ack, ach, poxB) strain was transformed by the electric pulse method. The transformed strain was spread on a CM-Dex agar medium containing 25 μg/ml kanamycin (containing 1.5% agar in 5 g/L glucose, 10 g/L polypeptone, 10 g/L yeast extract, 1 g/L $KH_2PO_4$, 0.4 g/L $MgSO_4.7H_2O$, 0.01 g/L $FeSO_4.7H_2O$, 0.01 g/L $MnSO_4.7H_2O$, 3 g/L urea, and 1.2 g/L soybean hydrolysate, and having a pH of 7.5 (KOH)), and cultured at 31.5° C. for about 24 hours. Then, the obtained colony was purified, and plasmid was extracted by a conventional method. As a result, it was confirmed that the target plasmid was introduced. A strain obtained by introducing the ODH-amplified plasmid into the strain in which acetic acid production is decreased was named 2256 Δ (ldh, pta, ack, ach, poxB)/pPKS-X. A strain obtained by introducing the vector was named 2256 Δ (ldh, pta, ack, ach, poxB)/pPK4.

(B) Production of Succinic Acid by the ODH-Amplified Strain

The strain in which the above-described ODH-amplified plasmid was introduced (2256 Δ (ldh, pta, ack, ach, poxB)/pPKS-X) and the strain in which the above-described vector was introduced (2256 Δ (ldh, pta, ack, ach, poxB)/pPK4) were cultured in CM-DEX agar medium. The obtained bacterial cells was inoculated in 3 ml of seed medium (20 g/L glucose, 14 g/L $(NH_4)_2SO_4$, 0.5 g/L $KH_2PO_4$, 0.5 g/L $K_2HPO_4$, 0.5 g/L $MgSO_4 \cdot 7H_2O$, 4 g/L urea, 0.02 g/L $FeSO_4 \cdot 7H_2O$, 0.02 g/L $MnSO_4 7H_2O$, 200 μg/L biotin, 200 μg/L VB1•HCl, 1 g/L yeast extract, and 1 g/L casamino acid). The bacterial cells were cultured in test tubes at 31.5° C. for about 8 hours under an aerobic condition with shaking.

After that, 3 ml each of the main medium (200 g/L glucose was filtered, and magnesium carbonate sterilized with dry heat was mixed with the filtered glucose so as to attain a final concentration of 143 g/L) was added in each of the test tubes. The test tubes were sealed with silicon corks to prevent aeration, and were subjected to culturing for succinic acid production at 31.5° C. for about 48 hours with shaking. The amount of produced succinic acid was analyzed by liquid chromatography. As a column, 2 pieces of Rezex ROA-Organic Acid $H^+$ (Phenomenex Inc.) tandemly linked with each other were used, and samples were eluted with 5 mM p-toluenesulfonic acid at 50° C. The eluate was neutralized with 20 mM Bis-Tris aqueous solution containing 5 mM p-toluenesulfonic acid and 100 μM EDTA. Electric conductivity of the mixture was measured by CDD-10AD (Shimadzu Corporation) to measure succinic acid. Multiple specimens of each bacterial strain were subjected to evaluation, and the average results are shown in Table 1. Yield (%) shows a yield of succinic acid with respect to glucose, and α-KG/SA (%) shows a concentration ratio of α-ketoglutarate (α-KG) to succinic acid (SA) in the culture medium.

TABLE 1

Production of succinic acid by the ODH-enhanced strain

| Name of bacterial strain | Yield (%) | α-KG/SA (%) |
|---|---|---|
| 2256Δ (ldh, pta, ack, poxB, ach)/(pPK4) | 48.7 | 3.0 |
| 2256Δ (ldh, pta, ack, poxB, ach)/(pPKS-X) | 51.4 | 1.6 |

In 2256 Δ (ldh, pta, ack, poxB, ach)/(pPKS-X) strain as the ODH-amplified strain, the yield increased by about 3% in average, and the amount of α-KG as a by-product decreased to about half in comparison with those of 2256 Δ (ldh, pta, ack, poxB, ach)/(pPK4) as the control. From these results, it was found that, in a succinic acid-producing bacterium which was modified so that acetic acid production was decreased, enhancement of an ODH activity contributed to decrease in production of α-KG as a by-product and increase in succinic acid production.

INDUSTRIAL APPLICABILITY

According to the production method of the present invention, an organic acid such as succinic acid can be rapidly produced with high efficiency. The obtained organic acid such as succinic acid can be used as food additives, or in pharmaceuticals, cosmetics, and the like. Besides, an organic acid-containing polymer can also be produced by a polymerization reaction using the obtained organic acid as a raw material.

The invention claimed is:

1. A coryneform bacterium having succinic acid-producing ability, wherein said bacterium is modified so that 2-oxoglutarate dehydrogenase activity is enhanced as compared with the corresponding unmodified bacterium by placing a gene encoding 2-oxoglutarate dehydrogenase under the control of a strong heterologous promoter or by increasing the copy number of said gene,
   wherein said gene encoding 2-oxoglutarate dehydrogenase has a nucleotide sequence not less than 95% homologous to SEQ ID NO: 3, and
   wherein the bacterium is further modified so that lactate dehydrogenase activity is decreased by introducing a deletion or insertion in a gene encoding lactate dehydrogenase, and pyruvate carboxylase activity is enhanced by placing a gene encoding pyruvate carboxylase under the control of a strong heterologous promoter or by increasing the copy number of said gene.

2. A coryneform bacterium having succinic acid-producing ability, wherein said bacterium is modified so that acetic acid production is decreased by decreasing
   (a) one of or both of acetate kinase activity and phosphotransacetylase activity,
   (b) acetyl-CoA hydrolase activity, and
   (c) pyruvate oxidase activity,
   by introducing a deletion or insertion in a gene encoding each enzyme, and 2-oxoglutarate dehydrogenase activity is enhanced as compared with the corresponding unmodified bacterium by placing a gene encoding 2-oxoglutarate dehydrogenase under the control of a strong heterologous promoter or by increasing the copy number of said gene, and
   wherein said gene encoding 2-oxoglutarate dehydrogenase has a nucleotide sequence not less than 95% homologous to SEQ ID NO: 3, and
   wherein the bacterium is further modified so that lactate dehydrogenase activity is decreased by introducing a deletion or insertion in a gene encoding lactate dehydrogenase.

3. The coryneform bacterium according to claim 2, wherein the bacterium is further modified so that pyruvate carboxylase activity is enhanced by placing a gene encoding pyruvate carboxylase under the control of a strong heterologous promoter or by increasing the copy number of said gene.

4. A method for producing succinic acid, comprising:
allowing the coryneform bacterium according to any one of claims 1, 2 and 3 or a treated cell thereof to act on an organic raw material under anaerobic atmosphere in a reaction solution containing a carbonate ion, a bicarbonate ion, or carbon dioxide gas to thereby produce succinic acid; and
collecting the succinic acid.

5. The method according to claim 4, wherein the organic raw material is glucose or sucrose.

6. A method for producing a succinic acid-containing polymer, comprising:
producing succinic acid by the method according to claim 4; and
subjecting the obtained succinic acid as a raw material to a polymerization reaction.

* * * * *

SEQUENCE LISTING

```
<160> NUMBER OF SEQ ID NOS: 17

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagcatcgc cgacaacatt ggctacggat g                           31

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcacagattc gtttcatacc ttccacctta ggcaacca                    38

<210> SEQ ID NO 3
<211> LENGTH: 3774
<212> TYPE: DNA
<213> ORGANISM: Brevibacterium flavum
<220> FEATURE:
<221> NAME/KEY: CDS
```

<222> LOCATION: (1)..(3771)

<400> SEQUENCE: 3

| atg | cta | caa | ctg | ggg | ctt | agg | cat | aat | cag | cca | acg | acc | aac | gtt | aca | 48 |
|---|---|---|---|---|---|---|---|---|---|---|---|---|---|---|---|---|
| Met | Leu | Gln | Leu | Gly | Leu | Arg | His | Asn | Gln | Pro | Thr | Thr | Asn | Val | Thr | |
| 1 | | | | 5 | | | | | 10 | | | | | 15 | | |

| gtg | gat | aaa | aca | aag | ctc | aat | aaa | ccc | tca | aga | agc | aag | gaa | aag | agg | 96 |
|---|---|---|---|---|---|---|---|---|---|---|---|---|---|---|---|---|
| Val | Asp | Lys | Thr | Lys | Leu | Asn | Lys | Pro | Ser | Arg | Ser | Lys | Glu | Lys | Arg | |
| | | | 20 | | | | | 25 | | | | | 30 | | | |

| cga | gta | cct | gcc | gtg | agc | agc | gct | agt | act | ttc | ggc | cag | aat | gcg | tgg | 144 |
|---|---|---|---|---|---|---|---|---|---|---|---|---|---|---|---|---|
| Arg | Val | Pro | Ala | Val | Ser | Ser | Ala | Ser | Thr | Phe | Gly | Gln | Asn | Ala | Trp | |
| | | 35 | | | | | 40 | | | | | 45 | | | | |

| ctg | gta | gac | gag | atg | ttc | cag | cag | ttc | cag | aag | gac | ccc | aag | tcc | gtg | 192 |
|---|---|---|---|---|---|---|---|---|---|---|---|---|---|---|---|---|
| Leu | Val | Asp | Glu | Met | Phe | Gln | Gln | Phe | Gln | Lys | Asp | Pro | Lys | Ser | Val | |
| 50 | | | | | 55 | | | | | 60 | | | | | | |

| gac | aag | gaa | tgg | aga | gaa | ctc | ttt | gag | gcg | cag | ggg | gga | cca | aat | act | 240 |
|---|---|---|---|---|---|---|---|---|---|---|---|---|---|---|---|---|
| Asp | Lys | Glu | Trp | Arg | Glu | Leu | Phe | Glu | Ala | Gln | Gly | Gly | Pro | Asn | Thr | |
| 65 | | | | 70 | | | | | 75 | | | | | 80 | | |

| acc | ccc | gct | aca | aca | gaa | gca | cag | cct | tca | gcg | ccc | aag | gag | tct | gcg | 288 |
|---|---|---|---|---|---|---|---|---|---|---|---|---|---|---|---|---|
| Thr | Pro | Ala | Thr | Thr | Glu | Ala | Gln | Pro | Ser | Ala | Pro | Lys | Glu | Ser | Ala | |
| | | | | 85 | | | | | 90 | | | | | 95 | | |

| aaa | cca | gca | cca | aag | gct | gcc | cct | gca | gcc | aag | gca | gca | ccg | cgc | gta | 336 |
|---|---|---|---|---|---|---|---|---|---|---|---|---|---|---|---|---|
| Lys | Pro | Ala | Pro | Lys | Ala | Ala | Pro | Ala | Ala | Lys | Ala | Ala | Pro | Arg | Val | |
| | | | 100 | | | | | 105 | | | | | 110 | | | |

| gaa | acc | aag | ccg | gcc | gac | aag | acc | gcc | cct | aag | gcc | aag | gag | tcc | tca | 384 |
|---|---|---|---|---|---|---|---|---|---|---|---|---|---|---|---|---|
| Glu | Thr | Lys | Pro | Ala | Asp | Lys | Thr | Ala | Pro | Lys | Ala | Lys | Glu | Ser | Ser | |
| | | 115 | | | | | 120 | | | | | 125 | | | | |

| gtg | cca | cag | caa | cct | aag | ctt | ccg | gag | cca | gga | caa | acc | cca | atc | agg | 432 |
|---|---|---|---|---|---|---|---|---|---|---|---|---|---|---|---|---|
| Val | Pro | Gln | Gln | Pro | Lys | Leu | Pro | Glu | Pro | Gly | Gln | Thr | Pro | Ile | Arg | |
| | 130 | | | | | 135 | | | | | 140 | | | | | |

| ggt | att | ttc | aag | tcc | atc | gcg | aag | aac | atg | gat | atc | tcc | ctg | gaa | atc | 480 |
|---|---|---|---|---|---|---|---|---|---|---|---|---|---|---|---|---|
| Gly | Ile | Phe | Lys | Ser | Ile | Ala | Lys | Asn | Met | Asp | Ile | Ser | Leu | Glu | Ile | |
| 145 | | | | | 150 | | | | | 155 | | | | | 160 | |

| cca | acc | gca | acc | tcg | gtt | cgc | gat | atg | cca | gct | cgc | ctc | atg | ttc | gaa | 528 |
|---|---|---|---|---|---|---|---|---|---|---|---|---|---|---|---|---|
| Pro | Thr | Ala | Thr | Ser | Val | Arg | Asp | Met | Pro | Ala | Arg | Leu | Met | Phe | Glu | |
| | | | | 165 | | | | | 170 | | | | | 175 | | |

| aac | cgc | gcg | atg | gtc | aac | gat | cag | ctc | aag | cgc | acc | cgc | ggt | ggc | aag | 576 |
|---|---|---|---|---|---|---|---|---|---|---|---|---|---|---|---|---|
| Asn | Arg | Ala | Met | Val | Asn | Asp | Gln | Leu | Lys | Arg | Thr | Arg | Gly | Gly | Lys | |
| | | | 180 | | | | | 185 | | | | | 190 | | | |

| atc | tcc | ttc | acc | cac | atc | att | ggc | tac | gcc | atg | gtg | aag | gca | gtc | atg | 624 |
|---|---|---|---|---|---|---|---|---|---|---|---|---|---|---|---|---|
| Ile | Ser | Phe | Thr | His | Ile | Ile | Gly | Tyr | Ala | Met | Val | Lys | Ala | Val | Met | |
| | | 195 | | | | | 200 | | | | | 205 | | | | |

| gct | cac | ccg | gac | atg | aac | aac | tcc | tac | gac | gtc | atc | gac | ggc | aag | cca | 672 |
|---|---|---|---|---|---|---|---|---|---|---|---|---|---|---|---|---|
| Ala | His | Pro | Asp | Met | Asn | Asn | Ser | Tyr | Asp | Val | Ile | Asp | Gly | Lys | Pro | |
| | | | | 210 | | | | | 215 | | | | | 220 | | |

| acc | ctg | atc | gtg | cct | gag | cac | atc | aac | ctg | ggc | ctt | gct | atc | gac | ctt | 720 |
|---|---|---|---|---|---|---|---|---|---|---|---|---|---|---|---|---|
| Thr | Leu | Ile | Val | Pro | Glu | His | Ile | Asn | Leu | Gly | Leu | Ala | Ile | Asp | Leu | |
| 225 | | | | | 230 | | | | | 235 | | | | | 240 | |

| cct | cag | aag | gac | ggc | tcc | cgc | gca | ctt | gtc | gta | gca | gcc | atc | aag | gaa | 768 |
|---|---|---|---|---|---|---|---|---|---|---|---|---|---|---|---|---|
| Pro | Gln | Lys | Asp | Gly | Ser | Arg | Ala | Leu | Val | Val | Ala | Ala | Ile | Lys | Glu | |
| | | | | 245 | | | | | 250 | | | | | 255 | | |

| acc | gag | aag | atg | aac | ttc | tcc | gag | ttc | ctc | gca | gcc | tac | gaa | gac | atc | 816 |
|---|---|---|---|---|---|---|---|---|---|---|---|---|---|---|---|---|
| Thr | Glu | Lys | Met | Asn | Phe | Ser | Glu | Phe | Leu | Ala | Ala | Tyr | Glu | Asp | Ile | |
| | | | 260 | | | | | 265 | | | | | 270 | | | |

| gtg | gca | cgc | tcc | cgc | aag | ggc | aag | ctc | acc | atg | gat | gac | tac | cag | ggc | 864 |
|---|---|---|---|---|---|---|---|---|---|---|---|---|---|---|---|---|
| Val | Ala | Arg | Ser | Arg | Lys | Gly | Lys | Leu | Thr | Met | Asp | Asp | Tyr | Gln | Gly | |
| | | 275 | | | | | 280 | | | | | 285 | | | | |

| gtt | acc | gtt | tcc | ttg | acc | aac | cca | ggt | ggc | atc | ggt | acc | cgc | cac | tct | 912 |
|---|---|---|---|---|---|---|---|---|---|---|---|---|---|---|---|---|
| Val | Thr | Val | Ser | Leu | Thr | Asn | Pro | Gly | Gly | Ile | Gly | Thr | Arg | His | Ser | |
| | 290 | | | | | 295 | | | | | 300 | | | | | |

```
gtt cca cgt cta acc aag ggc cag ggc acc atc atc ggt gtc ggt tcc      960
Val Pro Arg Leu Thr Lys Gly Gln Gly Thr Ile Ile Gly Val Gly Ser
305                 310                 315                 320 atg gat tac cca gca gag ttc cag ggc gct tca gaa gac cgc ctt gca     1008
Met Asp Tyr Pro Ala Glu Phe Gln Gly Ala Ser Glu Asp Arg Leu Ala
                325                 330                 335 gag ctc ggc gtt ggc aaa ctt gtc acc atc acc tcc acc tac gat cac     1056
Glu Leu Gly Val Gly Lys Leu Val Thr Ile Thr Ser Thr Tyr Asp His
            340                 345                 350 cgc gtg atc cag ggt gct gtg tcc ggt gaa ttc ctg cgc acc atg tct     1104
Arg Val Ile Gln Gly Ala Val Ser Gly Glu Phe Leu Arg Thr Met Ser
        355                 360                 365 cgc ctg ctc acc gat gat tcc ttc tgg gat gag atc ttc gac gca atg     1152
Arg Leu Leu Thr Asp Asp Ser Phe Trp Asp Glu Ile Phe Asp Ala Met
    370                 375                 380 aac gtt cct tac acc cca atg cgt tgg gca cag gac gtt cca aac acc     1200
Asn Val Pro Tyr Thr Pro Met Arg Trp Ala Gln Asp Val Pro Asn Thr
385                 390                 395                 400 ggt gtt gat aag aac acc cgc gtc atg cag ctc att gag gca tac cgc     1248
Gly Val Asp Lys Asn Thr Arg Val Met Gln Leu Ile Glu Ala Tyr Arg
                405                 410                 415 tcc cgt gga cac ctc atc gct gac acc aac cca ctt tca tgg gtt cag     1296
Ser Arg Gly His Leu Ile Ala Asp Thr Asn Pro Leu Ser Trp Val Gln
                420                 425                 430 cct ggc atg cca gtt cca gac cac cgc gac ctc gac atc gag acc cac     1344
Pro Gly Met Pro Val Pro Asp His Arg Asp Leu Asp Ile Glu Thr His
            435                 440                 445 aac ctg acc atc tgg gat ctg gac cgt acc ttc aac gtc ggt ggc ttc     1392
Asn Leu Thr Ile Trp Asp Leu Asp Arg Thr Phe Asn Val Gly Gly Phe
        450                 455                 460 ggc ggc aag gag acc atg acc ctg cgc gag gta ctg tcc cgc ctc cgc     1440
Gly Gly Lys Glu Thr Met Thr Leu Arg Glu Val Leu Ser Arg Leu Arg
465                 470                 475                 480 gct gcg tac acc ctc aag gtc ggc tcc gaa tac acc cac atc ctg gac     1488
Ala Ala Tyr Thr Leu Lys Val Gly Ser Glu Tyr Thr His Ile Leu Asp
                485                 490                 495 cgc gac gag cgc acc tgg ctg cag gac cgc ctc gag gcc gga atg cca     1536
Arg Asp Glu Arg Thr Trp Leu Gln Asp Arg Leu Glu Ala Gly Met Pro
                500                 505                 510 aag cca acc cag gca gag cag aag tac atc ctg cag aag ctg aac gcc     1584
Lys Pro Thr Gln Ala Glu Gln Lys Tyr Ile Leu Gln Lys Leu Asn Ala
            515                 520                 525 gcg gag gct ttc gag aac ttc ctg cag acc aag tac gtc ggc cag aag     1632
Ala Glu Ala Phe Glu Asn Phe Leu Gln Thr Lys Tyr Val Gly Gln Lys
        530                 535                 540 cgc ttc tcc ctc gaa ggt gca gaa gca ctt atc cca ctg atg gac tcc     1680
Arg Phe Ser Leu Glu Gly Ala Glu Ala Leu Ile Pro Leu Met Asp Ser
545                 550                 555                 560 gcc atc gac acc gcc gca ggc caa ggc ctc gac gaa gtt gtc atc ggt     1728
Ala Ile Asp Thr Ala Ala Gly Gln Gly Leu Asp Glu Val Val Ile Gly
                565                 570                 575 atg cca cac cgt ggt cgc ctc aac gtg ctg ttc aac atc gtg ggc aag     1776
Met Pro His Arg Gly Arg Leu Asn Val Leu Phe Asn Ile Val Gly Lys
                580                 585                 590 cca ctg gca tcc atc ttc aac gag ttt gaa ggc caa atg gag cag ggc     1824
Pro Leu Ala Ser Ile Phe Asn Glu Phe Glu Gly Gln Met Glu Gln Gly
            595                 600                 605 cag atc ggt ggc tcc ggt gac gtg aag tac cac ctc ggt tcc gaa ggc     1872
Gln Ile Gly Gly Ser Gly Asp Val Lys Tyr His Leu Gly Ser Glu Gly
        610                 615                 620
```

```
                                          -continued
cag cac ctg cag atg ttc ggc gac ggc gag atc aag gtc tcc ctg act   1920
Gln His Leu Gln Met Phe Gly Asp Gly Glu Ile Lys Val Ser Leu Thr
625                 630                 635                 640 gct aac ccg tcc cac ctg gaa gct gtt aac cca gtg atg gaa ggt atc   1968
Ala Asn Pro Ser His Leu Glu Ala Val Asn Pro Val Met Glu Gly Ile
            645                 650                 655 gtc cgc gca aag cag gac tac ctg gac aag ggc gta gac ggc aag act   2016
Val Arg Ala Lys Gln Asp Tyr Leu Asp Lys Gly Val Asp Gly Lys Thr
        660                 665                 670 gtt gtg cca ctg ctg ctc cac ggt gac gct gca ttc gca ggc ctg ggc   2064
Val Val Pro Leu Leu Leu His Gly Asp Ala Ala Phe Ala Gly Leu Gly
    675                 680                 685 atc gtg cca gaa acc atc aac ctg gct aag ctg cgt ggc tac gac gtc   2112
Ile Val Pro Glu Thr Ile Asn Leu Ala Lys Leu Arg Gly Tyr Asp Val
690                 695                 700 ggc ggc acc atc cac atc gtg gtg aac aac cag atc ggc ttc acc acc   2160
Gly Gly Thr Ile His Ile Val Val Asn Asn Gln Ile Gly Phe Thr Thr
705                 710                 715                 720 acc cca gac tcc agc cgc tcc atg cac tac gca acc gac tac gcc aag   2208
Thr Pro Asp Ser Ser Arg Ser Met His Tyr Ala Thr Asp Tyr Ala Lys
            725                 730                 735 gca ttc ggc tgc cca gtc ttc cac gtc aac ggc gac gac cca gag gca   2256
Ala Phe Gly Cys Pro Val Phe His Val Asn Gly Asp Asp Pro Glu Ala
        740                 745                 750 gtt gtc tgg gtt ggc cag ctg gcc acc gag tac cgt cgc cgc ttc ggc   2304
Val Val Trp Val Gly Gln Leu Ala Thr Glu Tyr Arg Arg Arg Phe Gly
    755                 760                 765 aag gac gtc ttc atc gac ctc gtc tgc tac cgc ctc cgc ggc cac aac   2352
Lys Asp Val Phe Ile Asp Leu Val Cys Tyr Arg Leu Arg Gly His Asn
770                 775                 780 gaa gct gat gat cct tcc atg acc cag cca aag atg tat gag ctc atc   2400
Glu Ala Asp Asp Pro Ser Met Thr Gln Pro Lys Met Tyr Glu Leu Ile
785                 790                 795                 800 acc ggc cgc gag acc gtt cgt gct cag tac acc gaa gac ctg ctc gga   2448
Thr Gly Arg Glu Thr Val Arg Ala Gln Tyr Thr Glu Asp Leu Leu Gly
            805                 810                 815 cgt gga gac ctc tcc aac gaa gat gca gaa gca gtc gtc cgc gac ttc   2496
Arg Gly Asp Leu Ser Asn Glu Asp Ala Glu Ala Val Val Arg Asp Phe
        820                 825                 830 cac gac cag atg gaa tct gtg ttc aac gaa gtc aag gaa ggc ggc aag   2544
His Asp Gln Met Glu Ser Val Phe Asn Glu Val Lys Glu Gly Gly Lys
    835                 840                 845 aag cag gct gag gca cag acc ggc atc acc ggc tcc cag aag ctt cca   2592
Lys Gln Ala Glu Ala Gln Thr Gly Ile Thr Gly Ser Gln Lys Leu Pro
850                 855                 860 cac ggc ctt gag acc aac atc tcc cgt gaa gag ctc ctg gaa ctg gga   2640
His Gly Leu Glu Thr Asn Ile Ser Arg Glu Glu Leu Leu Glu Leu Gly
865                 870                 875                 880 cag gct ttc gcc aac acc cca gaa ggc ttc aac tac cac cca cgt gtg   2688
Gln Ala Phe Ala Asn Thr Pro Glu Gly Phe Asn Tyr His Pro Arg Val
            885                 890                 895 gct ccc gtt gct aag aag cgc gtc tcc tct gtc acc gaa ggt ggc atc   2736
Ala Pro Val Ala Lys Lys Arg Val Ser Ser Val Thr Glu Gly Gly Ile
        900                 905                 910 gac tgg gca tgg ggc gag ctc ctc gcc ttc ggt tcc ctg gct aac tcc   2784
Asp Trp Ala Trp Gly Glu Leu Leu Ala Phe Gly Ser Leu Ala Asn Ser
    915                 920                 925 ggc cgc ttg gtt cgc ctt gca ggt gaa gat tcc cgc cgc ggt acc ttc   2832
Gly Arg Leu Val Arg Leu Ala Gly Glu Asp Ser Arg Arg Gly Thr Phe
930                 935                 940
```

```
acc cag cgc cac gca gtt gcc atc gac cca gcg acc gct gaa gag ttc    2880
Thr Gln Arg His Ala Val Ala Ile Asp Pro Ala Thr Ala Glu Glu Phe
945                 950                 955                 960 aac cca ctc cac gag ctt gca cag tcc aag ggc aac aac ggt aag ttc    2928
Asn Pro Leu His Glu Leu Ala Gln Ser Lys Gly Asn Asn Gly Lys Phe
                965                 970                 975 ctg gtc tac aac tcc gca ctg acc gag tac gca ggc atg ggc ttc gag    2976
Leu Val Tyr Asn Ser Ala Leu Thr Glu Tyr Ala Gly Met Gly Phe Glu
            980                 985                 990 tac ggc tac tcc gta gga aac gaa gac tcc atc gtt gca tgg gaa gca    3024
Tyr Gly Tyr Ser Val Gly Asn Glu Asp Ser Ile Val Ala Trp Glu Ala
        995                 1000                1005 cag ttc ggc gac ttc gcc aac ggc gct cag acc atc atc gat gag        3069
Gln Phe Gly Asp Phe Ala Asn Gly Ala Gln Thr Ile Ile Asp Glu
    1010                1015                1020 tac gtc tcc tca ggc gaa gct aag tgg ggc cag acc tcc aag ctg        3114
Tyr Val Ser Ser Gly Glu Ala Lys Trp Gly Gln Thr Ser Lys Leu
1025                1030                1035 atc ctt ctg ctg cct cac ggc tac gaa ggc cag ggc cca gac cac        3159
Ile Leu Leu Leu Pro His Gly Tyr Glu Gly Gln Gly Pro Asp His
    1040                1045                1050 tct tcc gca cgt atc gag cgc ttc ctg cag ctg tgc gct gag ggt        3204
Ser Ser Ala Arg Ile Glu Arg Phe Leu Gln Leu Cys Ala Glu Gly
    1055                1060                1065 tcc atg act gtt gct cag cca tcc acc cca gca aac cac ttc cac        3249
Ser Met Thr Val Ala Gln Pro Ser Thr Pro Ala Asn His Phe His
1070                1075                1080 cta ctg cgt cgt cac gct ctg tcc gac ctg aag cgt cca ctg gtt        3294
Leu Leu Arg Arg His Ala Leu Ser Asp Leu Lys Arg Pro Leu Val
    1085                1090                1095 atc ttc acc ccg aag tcc atg ctg cgt aac aag gct gct gcc tcc        3339
Ile Phe Thr Pro Lys Ser Met Leu Arg Asn Lys Ala Ala Ala Ser
1100                1105                1110 gca cca gaa gac ttc act gag gtc acc aag ttc cag tcc gtg atc        3384
Ala Pro Glu Asp Phe Thr Glu Val Thr Lys Phe Gln Ser Val Ile
    1115                1120                1125 aac gat cca aac gtt gca gat gca gcc aag gtg aag aag gtc atg        3429
Asn Asp Pro Asn Val Ala Asp Ala Ala Lys Val Lys Lys Val Met
    1130                1135                1140 ctg gtc tcc ggc aag ctg tac tac gaa ttg gca aag cgc aag gag        3474
Leu Val Ser Gly Lys Leu Tyr Tyr Glu Leu Ala Lys Arg Lys Glu
    1145                1150                1155 aag gac gga cgc gac gac atc gcg atc gtt cgt atc gaa atg ctc        3519
Lys Asp Gly Arg Asp Asp Ile Ala Ile Val Arg Ile Glu Met Leu
1160                1165                1170 cac cca att ccg ttc aac cgc atc tcc gag gct ctt gcc ggc tac        3564
His Pro Ile Pro Phe Asn Arg Ile Ser Glu Ala Leu Ala Gly Tyr
    1175                1180                1185 cct aac gct gag gaa gtc ctc ttc gtt cag gat gag cca gca aac        3609
Pro Asn Ala Glu Glu Val Leu Phe Val Gln Asp Glu Pro Ala Asn
    1190                1195                1200 cag ggc cca tgg ccg ttc tac cag gag cac ctc cca gag ctg atc        3654
Gln Gly Pro Trp Pro Phe Tyr Gln Glu His Leu Pro Glu Leu Ile
1205                1210                1215 ccg aac atg cca aag atg cgc cgc gtt tcc cgc cgc gct cag tcc        3699
Pro Asn Met Pro Lys Met Arg Arg Val Ser Arg Arg Ala Gln Ser
    1220                1225                1230 tcc acc gca act ggt gtt gcc aag gtg cac cag ctg gag gag aag        3744
Ser Thr Ala Thr Gly Val Ala Lys Val His Gln Leu Glu Glu Lys
    1235                1240                1245
```

```
cag ctt atc gac gag gct ttc gag gct taa                    3774
Gln Leu Ile Asp Glu Ala Phe Glu Ala
    1250              1255

<210> SEQ ID NO 4
<211> LENGTH: 1257
<212> TYPE: PRT
<213> ORGANISM: Brevibacterium flavum

<400> SEQUENCE: 4

Met Leu Gln Leu Gly Leu Arg His Asn Gln Pro Thr Thr Asn Val Thr
1               5                   10                  15

Val Asp Lys Thr Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Thr
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Asp Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Ala Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365
```

```
Arg Leu Leu Thr Asp Asp Ser Phe Trp Asp Glu Ile Phe Asp Ala Met
        370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Asn Leu Thr Ile Trp Asp Leu Asp Arg Thr Phe Asn Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
        515                 520                 525

Ala Glu Ala Phe Glu Asn Phe Leu Gln Thr Lys Tyr Val Gly Gln Lys
    530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
        595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu Leu His Gly Asp Ala Ala Phe Ala Gly Leu Gly
        675                 680                 685

Ile Val Pro Glu Thr Ile Asn Leu Ala Lys Leu Arg Gly Tyr Asp Val
    690                 695                 700

Gly Gly Thr Ile His Ile Val Val Asn Asn Gln Ile Gly Phe Thr Thr
705                 710                 715                 720

Thr Pro Asp Ser Ser Arg Ser Met His Tyr Ala Thr Asp Tyr Ala Lys
                725                 730                 735

Ala Phe Gly Cys Pro Val Phe His Val Asn Gly Asp Asp Pro Glu Ala
            740                 745                 750

Val Val Trp Val Gly Gln Leu Ala Thr Glu Tyr Arg Arg Arg Phe Gly
        755                 760                 765

Lys Asp Val Phe Ile Asp Leu Val Cys Tyr Arg Leu Arg Gly His Asn
    770                 775                 780

Glu Ala Asp Asp Pro Ser Met Thr Gln Pro Lys Met Tyr Glu Leu Ile
```

```
                785                 790                 795                 800
Thr Gly Arg Glu Thr Val Arg Ala Gln Tyr Thr Glu Asp Leu Leu Gly
                    805                 810                 815

Arg Gly Asp Leu Ser Asn Glu Asp Ala Glu Ala Val Val Arg Asp Phe
                820                 825                 830

His Asp Gln Met Glu Ser Val Phe Asn Glu Val Lys Glu Gly Gly Lys
                    835                 840                 845

Lys Gln Ala Glu Ala Gln Thr Gly Ile Thr Gly Ser Gln Lys Leu Pro
850                 855                 860

His Gly Leu Glu Thr Asn Ile Ser Arg Glu Glu Leu Leu Glu Leu Gly
865                 870                 875                 880

Gln Ala Phe Ala Asn Thr Pro Glu Gly Phe Asn Tyr His Pro Arg Val
                    885                 890                 895

Ala Pro Val Ala Lys Lys Arg Val Ser Val Thr Glu Gly Gly Ile
                900                 905                 910

Asp Trp Ala Trp Gly Glu Leu Leu Ala Phe Gly Ser Leu Ala Asn Ser
            915                 920                 925

Gly Arg Leu Val Arg Leu Ala Gly Glu Asp Ser Arg Arg Gly Thr Phe
        930                 935                 940

Thr Gln Arg His Ala Val Ala Ile Asp Pro Ala Thr Ala Glu Glu Phe
945                 950                 955                 960

Asn Pro Leu His Glu Leu Ala Gln Ser Lys Gly Asn Asn Gly Lys Phe
                    965                 970                 975

Leu Val Tyr Asn Ser Ala Leu Thr Glu Tyr Ala Gly Met Gly Phe Glu
                    980                 985                 990

Tyr Gly Tyr Ser Val Gly Asn Glu Asp Ser Ile Val Ala Trp Glu Ala
            995                 1000                1005

Gln Phe Gly Asp Phe Ala Asn Gly Ala Gln Thr Ile Ile Asp Glu
    1010                1015                1020

Tyr Val Ser Ser Gly Glu Ala Lys Trp Gly Gln Thr Ser Lys Leu
    1025                1030                1035

Ile Leu Leu Leu Pro His Gly Tyr Glu Gly Gln Gly Pro Asp His
    1040                1045                1050

Ser Ser Ala Arg Ile Glu Arg Phe Leu Gln Leu Cys Ala Glu Gly
    1055                1060                1065

Ser Met Thr Val Ala Gln Pro Ser Thr Pro Ala Asn His Phe His
    1070                1075                1080

Leu Leu Arg Arg His Ala Leu Ser Asp Leu Lys Arg Pro Leu Val
    1085                1090                1095

Ile Phe Thr Pro Lys Ser Met Leu Arg Asn Lys Ala Ala Ala Ser
    1100                1105                1110

Ala Pro Glu Asp Phe Thr Glu Val Thr Lys Phe Gln Ser Val Ile
    1115                1120                1125

Asn Asp Pro Asn Val Ala Asp Ala Ala Lys Val Lys Lys Val Met
    1130                1135                1140

Leu Val Ser Gly Lys Leu Tyr Tyr Glu Leu Ala Lys Arg Lys Glu
    1145                1150                1155

Lys Asp Gly Arg Asp Asp Ile Ala Ile Val Arg Ile Glu Met Leu
    1160                1165                1170

His Pro Ile Pro Phe Asn Arg Ile Ser Glu Ala Leu Ala Gly Tyr
    1175                1180                1185

Pro Asn Ala Glu Glu Val Leu Phe Val Gln Asp Glu Pro Ala Asn
    1190                1195                1200
```

```
Gln Gly  Pro Trp Pro Phe Tyr  Gln Glu His Leu Pro  Glu Leu Ile
    1205             1210              1215

Pro Asn  Met Pro Lys Met Arg  Arg Val Ser Arg  Ala Gln Ser
    1220             1225             1230

Ser Thr  Ala Thr Gly Val Ala  Lys Val His Gln Leu  Glu Glu Lys
    1235             1240              1245

Gln Leu  Ile Asp Glu Ala Phe  Glu Ala
    1250             1255

<210> SEQ ID NO 5
<211> LENGTH: 3423
<212> TYPE: DNA
<213> ORGANISM: Brevibacterium flavum
<220> FEATURE:
<221> NAME/KEY: CDS
<222> LOCATION: (1)..(3420)

<400> SEQUENCE: 5 atg tcg act cac aca tct tca acg ctt cca gca ttc aaa aag atc ttg     48
Met Ser Thr His Thr Ser Ser Thr Leu Pro Ala Phe Lys Lys Ile Leu
1               5                   10                  15 gta gca aac cgc ggc gaa atc gcg gtc cgt gct ttc cgt gca gca ctc     96
Val Ala Asn Arg Gly Glu Ile Ala Val Arg Ala Phe Arg Ala Ala Leu
            20                  25                  30 gaa acc ggt gca gcc acg gta gct att tac ccc cgt gaa gat cgg gga    144
Glu Thr Gly Ala Ala Thr Val Ala Ile Tyr Pro Arg Glu Asp Arg Gly
        35                  40                  45 tca ttc cac cgc tct ttt gct tct gaa gct gtc cgc att ggt act gaa    192
Ser Phe His Arg Ser Phe Ala Ser Glu Ala Val Arg Ile Gly Thr Glu
    50                  55                  60 ggc tca cca gtc aag gcg tac ctg gac atc gat gaa att atc ggt gca    240
Gly Ser Pro Val Lys Ala Tyr Leu Asp Ile Asp Glu Ile Ile Gly Ala
65                  70                  75                  80 gct aaa aaa gtt aaa gca gat gct att tac ccg gga tat ggc ttc ctg    288
Ala Lys Lys Val Lys Ala Asp Ala Ile Tyr Pro Gly Tyr Gly Phe Leu
                85                  90                  95 tct gaa aat gcc cag ctt gcc cgc gag tgc gcg gaa aac ggc att act    336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct    384
Phe Ile Gly Pro Thr Pro Glu Val Leu Asp Leu Thr Gly Asp Lys Ser
        115                 120                 125 cgt gcg gta acc gcc gcg aag aag gct ggt ctg cca gtt ttg gcg gaa    432
Arg Ala Val Thr Ala Ala Lys Lys Ala Gly Leu Pro Val Leu Ala Glu
    130                 135                 140 tcc acc ccg agc aaa aac atc gat gac atc gtt aaa agc gct gaa ggc    480
Ser Thr Pro Ser Lys Asn Ile Asp Asp Ile Val Lys Ser Ala Glu Gly
145                 150                 155                 160 cag act tac ccc atc ttt gta aag gca gtt gcc ggt ggt ggc gga cgc    528
Gln Thr Tyr Pro Ile Phe Val Lys Ala Val Ala Gly Gly Gly Gly Arg
                165                 170                 175 ggt atg cgc ttt gtt tct tca cct gat gag ctt cgc aaa ttg gca aca    576
Gly Met Arg Phe Val Ser Ser Pro Asp Glu Leu Arg Lys Leu Ala Thr
            180                 185                 190 gaa gca tct cgt gaa gct gaa gcg gca ttc ggc gac ggt tcg gta tat    624
Glu Ala Ser Arg Glu Ala Glu Ala Ala Phe Gly Asp Gly Ser Val Tyr
        195                 200                 205 gtc gag cgt gct gtg att aac ccc cag cac att gaa gtg cag atc ctt    672
Val Glu Arg Ala Val Ile Asn Pro Gln His Ile Glu Val Gln Ile Leu
    210                 215                 220 ggc gat cgc act gga gaa gtt gta cac ctt tat gaa cgt gac tgc tca    720
Gly Asp Arg Thr Gly Glu Val Val His Leu Tyr Glu Arg Asp Cys Ser
```

```
Gly Asp Arg Thr Gly Glu Val Val His Leu Tyr Glu Arg Asp Cys Ser
225                 230                 235                 240 ctg cag cgt cgt cac caa aaa gtt gtc gaa att gcg cca gca cag cat      768
Leu Gln Arg Arg His Gln Lys Val Val Glu Ile Ala Pro Ala Gln His
            245                 250                 255 ttg gat cca gaa ctg cgt gat cgc att tgt gcg gat gca gta aag ttc      816
Leu Asp Pro Glu Leu Arg Asp Arg Ile Cys Ala Asp Ala Val Lys Phe
        260                 265                 270 tgc cgc tcc att ggt tac cag ggc gcg gga act gtg gaa ttc ttg gtc      864
Cys Arg Ser Ile Gly Tyr Gln Gly Ala Gly Thr Val Glu Phe Leu Val
    275                 280                 285 gat gaa aag ggc aac cac gtt ttc atc gaa atg aac cca cgt atc cag      912
Asp Glu Lys Gly Asn His Val Phe Ile Glu Met Asn Pro Arg Ile Gln
290                 295                 300 gtt gag cac acc gtg act gaa gaa gtc acc gag gtg gac ctg gtg aag      960
Val Glu His Thr Val Thr Glu Glu Val Thr Glu Val Asp Leu Val Lys
305                 310                 315                 320 gcg cag atg cgc ttg gct gct ggt gca acc ttg aag gaa ttg ggt ctg     1008
Ala Gln Met Arg Leu Ala Ala Gly Ala Thr Leu Lys Glu Leu Gly Leu
                325                 330                 335 acc caa gat aag atc aag acc cac ggt gcg gca ctg cag tgc cgc atc     1056
Thr Gln Asp Lys Ile Lys Thr His Gly Ala Ala Leu Gln Cys Arg Ile
            340                 345                 350 acc acg gaa gat cca aac aac ggc ttc cgc cca gat acc gga act atc     1104
Thr Thr Glu Asp Pro Asn Asn Gly Phe Arg Pro Asp Thr Gly Thr Ile
        355                 360                 365 acc gcg tac cgc tca cca ggc gga gct ggc gtt cgt ctt gac ggt gca     1152
Thr Ala Tyr Arg Ser Pro Gly Gly Ala Gly Val Arg Leu Asp Gly Ala
    370                 375                 380 gct cag ctc ggt ggc gaa atc acc gca cac ttt gac tcc atg ctg gtg     1200
Ala Gln Leu Gly Gly Glu Ile Thr Ala His Phe Asp Ser Met Leu Val
385                 390                 395                 400 aaa atg acc tgc cgt ggt tcc gat ttt gaa act gct gtt gct cgt gca     1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att     1296
Gln Arg Ala Leu Ala Glu Phe Thr Val Ser Gly Val Ala Thr Asn Ile
            420                 425                 430 ggt ttc ttg cgt gcg ttg ctg cgt gaa gag gac ttt act tcc aag cgc     1344
Gly Phe Leu Arg Ala Leu Leu Arg Glu Glu Asp Phe Thr Ser Lys Arg
        435                 440                 445 atc gcc acc gga ttt atc ggc gat cac cca cac ctc ctt cag gct cca     1392
Ile Ala Thr Gly Phe Ile Gly Asp His Pro His Leu Leu Gln Ala Pro
    450                 455                 460 cct gcg gat gat gag cag gga cgc atc ctg gat tac ttg gca gat gtc     1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gca cca     1488
Thr Val Asn Lys Pro His Gly Val Arg Pro Lys Asp Val Ala Ala Pro
                485                 490                 495 atc gat aag ctg ccc aac atc aag gat ctg cca ctg cca cgc ggt tcc     1536
Ile Asp Lys Leu Pro Asn Ile Lys Asp Leu Pro Leu Pro Arg Gly Ser
            500                 505                 510 cgt gac cgc ctg aag cag ctt gga cca gca gcg ttt gcc cgc gat ctc     1584
Arg Asp Arg Leu Lys Gln Leu Gly Pro Ala Ala Phe Ala Arg Asp Leu
        515                 520                 525 cgt gag cag gac gca ctg gca gtt act gat acc acc ttc cgc gat gca     1632
Arg Glu Gln Asp Ala Leu Ala Val Thr Asp Thr Thr Phe Arg Asp Ala
    530                 535                 540 cac cag tct ttg ctt gcg acc cga gtc cgc tca ttc gca ctg aag cct     1680
```

-continued

| | | | | | | | | | | | | | | | |
|---|---|---|---|---|---|---|---|---|---|---|---|---|---|---|---|
| His | Gln | Ser | Leu | Leu | Ala | Thr | Arg | Val | Arg | Ser | Phe | Ala | Leu | Lys | Pro |
| 545 | | | | 550 | | | | | 555 | | | | | 560 | |

| gcg | gca | gag | gcc | gtc | gca | aag | ctg | act | cct | gag | ctt | ttg | tcc | gtg | gag | 1728 |
|---|---|---|---|---|---|---|---|---|---|---|---|---|---|---|---|---|
| Ala | Ala | Glu | Ala | Val | Ala | Lys | Leu | Thr | Pro | Glu | Leu | Leu | Ser | Val | Glu | |
| | | | | 565 | | | | | 570 | | | | | 575 | | |

| gcc | tgg | ggc | ggt | gcg | acc | tac | gat | gtg | gcg | atg | cgt | ttc | ctc | ttt | gag | 1776 |
|---|---|---|---|---|---|---|---|---|---|---|---|---|---|---|---|---|
| Ala | Trp | Gly | Gly | Ala | Thr | Tyr | Asp | Val | Ala | Met | Arg | Phe | Leu | Phe | Glu | |
| | | | 580 | | | | | 585 | | | | | 590 | | | |

| gat | ccg | tgg | gac | agg | ctc | gac | gag | ctg | cgc | gag | gcg | atg | ccg | aat | gtg | 1824 |
|---|---|---|---|---|---|---|---|---|---|---|---|---|---|---|---|---|
| Asp | Pro | Trp | Asp | Arg | Leu | Asp | Glu | Leu | Arg | Glu | Ala | Met | Pro | Asn | Val | |
| | | 595 | | | | | 600 | | | | | 605 | | | | |

| aac | att | cag | atg | ctg | ctt | cgc | ggc | cgc | aac | acc | gtg | gga | tac | acc | cca | 1872 |
|---|---|---|---|---|---|---|---|---|---|---|---|---|---|---|---|---|
| Asn | Ile | Gln | Met | Leu | Leu | Arg | Gly | Arg | Asn | Thr | Val | Gly | Tyr | Thr | Pro | |
| 610 | | | | | 615 | | | | | 620 | | | | | | |

| tac | cca | gac | tcc | gtc | tgt | cgc | gcg | ttt | gtt | aag | gaa | gct | gcc | acc | tcc | 1920 |
|---|---|---|---|---|---|---|---|---|---|---|---|---|---|---|---|---|
| Tyr | Pro | Asp | Ser | Val | Cys | Arg | Ala | Phe | Val | Lys | Glu | Ala | Ala | Thr | Ser | |
| 625 | | | | | 630 | | | | | 635 | | | | | 640 | |

| ggc | gtg | gac | atc | ttc | cgc | atc | ttc | gac | gcg | ctt | aac | gac | gtc | tcc | cag | 1968 |
|---|---|---|---|---|---|---|---|---|---|---|---|---|---|---|---|---|
| Gly | Val | Asp | Ile | Phe | Arg | Ile | Phe | Asp | Ala | Leu | Asn | Asp | Val | Ser | Gln | |
| | | | | 645 | | | | | 650 | | | | | 655 | | |

| atg | cgt | cca | gca | atc | gac | gca | gtc | ctg | gag | acc | aac | acc | gcg | gtc | gct | 2016 |
|---|---|---|---|---|---|---|---|---|---|---|---|---|---|---|---|---|
| Met | Arg | Pro | Ala | Ile | Asp | Ala | Val | Leu | Glu | Thr | Asn | Thr | Ala | Val | Ala | |
| | | | 660 | | | | | 665 | | | | | 670 | | | |

| gaa | gtg | gct | atg | gct | tat | tct | ggt | gat | ctt | tcc | gat | ccg | aat | gaa | aag | 2064 |
|---|---|---|---|---|---|---|---|---|---|---|---|---|---|---|---|---|
| Glu | Val | Ala | Met | Ala | Tyr | Ser | Gly | Asp | Leu | Ser | Asp | Pro | Asn | Glu | Lys | |
| | | | 675 | | | | | 680 | | | | | 685 | | | |

| ctc | tac | acc | ctg | gat | tac | tac | ctg | aag | atg | gca | gag | gag | atc | gtc | aag | 2112 |
|---|---|---|---|---|---|---|---|---|---|---|---|---|---|---|---|---|
| Leu | Tyr | Thr | Leu | Asp | Tyr | Tyr | Leu | Lys | Met | Ala | Glu | Glu | Ile | Val | Lys | |
| | 690 | | | | | 695 | | | | | 700 | | | | | |

| tct | ggc | gct | cac | att | ctg | gct | att | aag | gat | atg | gct | ggt | ctg | ctt | cgc | 2160 |
|---|---|---|---|---|---|---|---|---|---|---|---|---|---|---|---|---|
| Ser | Gly | Ala | His | Ile | Leu | Ala | Ile | Lys | Asp | Met | Ala | Gly | Leu | Leu | Arg | |
| 705 | | | | 710 | | | | | 715 | | | | | 720 | | |

| cca | gct | gca | gcc | acc | aag | ctg | gtc | acc | gca | ctg | cgc | cgt | gaa | ttt | gat | 2208 |
|---|---|---|---|---|---|---|---|---|---|---|---|---|---|---|---|---|
| Pro | Ala | Ala | Ala | Thr | Lys | Leu | Val | Thr | Ala | Leu | Arg | Arg | Glu | Phe | Asp | |
| | | | 725 | | | | | 730 | | | | | 735 | | | |

| ctg | cca | gtg | cac | gtg | cac | acc | cac | gac | act | gcg | ggt | ggc | cag | ctg | gca | 2256 |
|---|---|---|---|---|---|---|---|---|---|---|---|---|---|---|---|---|
| Leu | Pro | Val | His | Val | His | Thr | His | Asp | Thr | Ala | Gly | Gly | Gln | Leu | Ala | |
| | | | 740 | | | | | 745 | | | | | 750 | | | |

| acc | tac | ttt | gct | gca | gct | caa | gct | ggt | gca | gat | gct | gtt | gac | ggt | gct | 2304 |
|---|---|---|---|---|---|---|---|---|---|---|---|---|---|---|---|---|
| Thr | Tyr | Phe | Ala | Ala | Ala | Gln | Ala | Gly | Ala | Asp | Ala | Val | Asp | Gly | Ala | |
| | | 755 | | | | | 760 | | | | | 765 | | | | |

| tcc | gca | cca | ctg | tct | ggc | acc | acc | tcc | cag | cca | tcc | ctg | tct | gcc | att | 2352 |
|---|---|---|---|---|---|---|---|---|---|---|---|---|---|---|---|---|
| Ser | Ala | Pro | Leu | Ser | Gly | Thr | Thr | Ser | Gln | Pro | Ser | Leu | Ser | Ala | Ile | |
| 770 | | | | 775 | | | | | 780 | | | | | | | |

| gtt | gct | gca | ttc | gcg | cac | acc | cgt | cgc | gat | acc | ggt | ttg | agc | ctc | gag | 2400 |
|---|---|---|---|---|---|---|---|---|---|---|---|---|---|---|---|---|
| Val | Ala | Ala | Phe | Ala | His | Thr | Arg | Arg | Asp | Thr | Gly | Leu | Ser | Leu | Glu | |
| 785 | | | | 790 | | | | | 795 | | | | | 800 | | |

| gct | gtt | tct | gac | ctc | gag | cca | tac | tgg | gaa | gca | gtg | cgc | gga | ctg | tac | 2448 |
|---|---|---|---|---|---|---|---|---|---|---|---|---|---|---|---|---|
| Ala | Val | Ser | Asp | Leu | Glu | Pro | Tyr | Trp | Glu | Ala | Val | Arg | Gly | Leu | Tyr | |
| | | | 805 | | | | | 810 | | | | | 815 | | | |

| ctg | cca | ttt | gag | tct | gga | acc | cca | ggc | cca | acc | ggt | cgc | gtc | tac | cgc | 2496 |
|---|---|---|---|---|---|---|---|---|---|---|---|---|---|---|---|---|
| Leu | Pro | Phe | Glu | Ser | Gly | Thr | Pro | Gly | Pro | Thr | Gly | Arg | Val | Tyr | Arg | |
| | | | 820 | | | | | 825 | | | | | 830 | | | |

| cac | gaa | atc | cca | ggc | gga | cag | ctg | tcc | aac | ctg | cgt | gca | cag | gcc | acc | 2544 |
|---|---|---|---|---|---|---|---|---|---|---|---|---|---|---|---|---|
| His | Glu | Ile | Pro | Gly | Gly | Gln | Leu | Ser | Asn | Leu | Arg | Ala | Gln | Ala | Thr | |
| | | 835 | | | | | 840 | | | | | 845 | | | | |

| gca | ctg | ggc | ctt | gcg | gat | cgt | ttc | gaa | ctc | atc | gaa | gac | aac | tac | gcg | 2592 |
|---|---|---|---|---|---|---|---|---|---|---|---|---|---|---|---|---|
| Ala | Leu | Gly | Leu | Ala | Asp | Arg | Phe | Glu | Leu | Ile | Glu | Asp | Asn | Tyr | Ala | |
| 850 | | | | 855 | | | | | 860 | | | | | | | |

| gca | gtt | aat | gag | atg | ctg | gga | cgc | cca | acc | aag | gtc | acc | cca | tcc | tcc | 2640 |
|---|---|---|---|---|---|---|---|---|---|---|---|---|---|---|---|---|

```
                Ala Val Asn Glu Met Leu Gly Arg Pro Thr Lys Val Thr Pro Ser Ser
                865                 870                 875                 880 aag gtt gtt ggc gac ctc gca ctc cac ctc gtt ggt gcg ggt gtg gat        2688
Lys Val Val Gly Asp Leu Ala Leu His Leu Val Gly Ala Gly Val Asp
                    885                 890                 895 cca gca gac ttt gct gca gat cca caa aag tac gac atc cca gac tct        2736
Pro Ala Asp Phe Ala Ala Asp Pro Gln Lys Tyr Asp Ile Pro Asp Ser
900                 905                 910 gtc atc gcg ttc ctg cgc ggc gag ctt ggt aac cct cca ggt ggc tgg        2784
Val Ile Ala Phe Leu Arg Gly Glu Leu Gly Asn Pro Pro Gly Gly Trp
            915                 920                 925 cca gag cca ctg cgc acc cgc gca ctg gaa ggc cgc tcc gaa ggc aag        2832
Pro Glu Pro Leu Arg Thr Arg Ala Leu Glu Gly Arg Ser Glu Gly Lys
        930                 935                 940 gca cct ctg acg gaa gtt cct gag gaa gag cag gcg cac ctc gac gct        2880
Ala Pro Leu Thr Glu Val Pro Glu Glu Glu Gln Ala His Leu Asp Ala
945                 950                 955                 960 gat gat tcc aag gaa cgt cgc aac agc ctc aac cgc ctg ctg ttc ccg        2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc        2976
Lys Pro Thr Glu Glu Phe Leu Glu His Arg Arg Arg Phe Gly Asn Thr
            980                 985                 990 tct gcg ctg gat gat cgt gaa ttc ttc tac ggc ctg gtc gaa ggc cgc       3024
Ser Ala Leu Asp Asp Arg Glu Phe Phe Tyr Gly Leu Val Glu Gly Arg
        995                 1000                1005 gag act ttg atc cgc ctg cca gat gtg cgc acc cca ctg ctt gtt           3069
Glu Thr Leu Ile Arg Leu Pro Asp Val Arg Thr Pro Leu Leu Val
    1010                1015                1020 cgc ctg gat gcg atc tcc gag cca gac gat aag ggt atg cgc aat          3114
Arg Leu Asp Ala Ile Ser Glu Pro Asp Asp Lys Gly Met Arg Asn
1025                1030                1035 gtt gtg gcc aac gtc aac ggc cag atc cgc cca atg cgt gtg cgt          3159
Val Val Ala Asn Val Asn Gly Gln Ile Arg Pro Met Arg Val Arg
        1040                1045                1050 gac cgc tcc gtt gag tct gtc acc gca acc gca gaa aag gca gat          3204
Asp Arg Ser Val Glu Ser Val Thr Ala Thr Ala Glu Lys Ala Asp
    1055                1060                1065 tcc tcc aac aag ggc cat gtt gct gca cca ttc gct ggt gtt gtc          3249
Ser Ser Asn Lys Gly His Val Ala Ala Pro Phe Ala Gly Val Val
1070                1075                1080 act gtg act gtt gct gaa ggt gat gag gtc aag gct gga gat gca          3294
Thr Val Thr Val Ala Glu Gly Asp Glu Val Lys Ala Gly Asp Ala
        1085                1090                1095 gtc gca atc atc gag gct atg aag atg gaa gca aca atc act gct          3339
Val Ala Ile Ile Glu Ala Met Lys Met Glu Ala Thr Ile Thr Ala
    1100                1105                1110 tct gtt gac ggc aaa atc gat cgc gtt gtg gtt cct gct gca acg          3384
Ser Val Asp Gly Lys Ile Asp Arg Val Val Val Pro Ala Ala Thr
1115                1120                1125 aag gtg gaa ggt ggc gac ttg atc gtc gtc gtt tcc taa                  3423
Lys Val Glu Gly Gly Asp Leu Ile Val Val Val Ser
        1130                1135                1140

<210> SEQ ID NO 6
<211> LENGTH: 1140
<212> TYPE: PRT
<213> ORGANISM: Brevibacterium flavum

<400> SEQUENCE: 6

Met Ser Thr His Thr Ser Ser Thr Leu Pro Ala Phe Lys Lys Ile Leu
```

```
1               5                   10                  15
Val Ala Asn Arg Gly Glu Ile Ala Val Arg Phe Arg Ala Ala Leu
                20                  25                  30

Glu Thr Gly Ala Ala Thr Val Ala Ile Tyr Pro Arg Glu Asp Arg Gly
         35                  40                  45

Ser Phe His Arg Ser Phe Ala Ser Glu Ala Val Arg Ile Gly Thr Glu
     50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                 85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ser Ser Pro Asp Glu Leu Arg Lys Leu Ala Thr
            180                 185                 190

Glu Ala Ser Arg Glu Ala Glu Ala Phe Gly Asp Gly Ser Val Tyr
        195                 200                 205

Val Glu Arg Ala Val Ile Asn Pro Gln His Ile Glu Val Gln Ile Leu
    210                 215                 220

Gly Asp Arg Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430
```

```
Gly Phe Leu Arg Ala Leu Leu Arg Glu Glu Asp Phe Thr Ser Lys Arg
            435                 440                 445

Ile Ala Thr Gly Phe Ile Gly Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Ala Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860
```

```
Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Ser
    1130                1135                1140

<210> SEQ ID NO 7
<211> LENGTH: 2579
<212> TYPE: DNA
<213> ORGANISM: Brevibacterium flavum
<220> FEATURE:
<221> NAME/KEY: CDS
<222> LOCATION: (1)..(1383)
<220> FEATURE:
<221> NAME/KEY: CDS
<222> LOCATION: (1386)..(2579)

<400> SEQUENCE: 7 atg tct gac aca ccg acc tca gct ctg atc acc acg gtc aac cgc agc      48
Met Ser Asp Thr Pro Thr Ser Ala Leu Ile Thr Thr Val Asn Arg Ser
1               5                   10                  15 ttc gat gga ttc gat ttg gaa gaa gta gca gca gac ctt gga gtt cgg      96
Phe Asp Gly Phe Asp Leu Glu Glu Val Ala Ala Asp Leu Gly Val Arg
                20                  25                  30 ctc acc tac ctg ccc gac gaa gaa cta gaa gta tcc aaa gtt ctc gcg     144
Leu Thr Tyr Leu Pro Asp Glu Glu Leu Glu Val Ser Lys Val Leu Ala
            35                  40                  45
```

```
gcg gac ctc ctc gct gag ggg cca gct ctc atc atc ggt gta gga aac      192
Ala Asp Leu Leu Ala Glu Gly Pro Ala Leu Ile Ile Gly Val Gly Asn
 50              55                  60 acg ttt ttc gac gcc cag gtc gcc gct gcc ctc ggc gtc cca gtg cta      240
Thr Phe Phe Asp Ala Gln Val Ala Ala Ala Leu Gly Val Pro Val Leu
 65              70                  75                  80 ctg ctg gta gac aag caa ggc aag cac gtt gct ctt gct cgc acc cag      288
Leu Leu Val Asp Lys Gln Gly Lys His Val Ala Leu Ala Arg Thr Gln
                 85                  90                  95 gta aac aat gcc ggc gca gtt gtt gca gca gca ttt acc gct gaa caa      336
Val Asn Asn Ala Gly Ala Val Val Ala Ala Ala Phe Thr Ala Glu Gln
            100                 105                 110 gag cca atg ccg gat aag ctg cgc aag gct gtg cgc aac cac agc aac      384
Glu Pro Met Pro Asp Lys Leu Arg Lys Ala Val Arg Asn His Ser Asn
        115                 120                 125 ctc gaa cca gtc atg agc gcc gaa ctc ttt gaa aac tgg ctg ctc aag      432
Leu Glu Pro Val Met Ser Ala Glu Leu Phe Glu Asn Trp Leu Leu Lys
130                 135                 140 cgc gca cgc gca gag cac tcc cac att gtg ctg cca gaa ggt gac gac      480
Arg Ala Arg Ala Glu His Ser His Ile Val Leu Pro Glu Gly Asp Asp
145                 150                 155                 160 gac cgc atc ttg atg gct gcc cac cag ctg ctt gat caa gac atc tgt      528
Asp Arg Ile Leu Met Ala Ala His Gln Leu Leu Asp Gln Asp Ile Cys
                165                 170                 175 gac atc acg atc ctg ggc gat cca gta aag atc aag gag cgc gct acc      576
Asp Ile Thr Ile Leu Gly Asp Pro Val Lys Ile Lys Glu Arg Ala Thr
            180                 185                 190 gaa ctt ggc ctg cac ctt aac act gca tac ctg gtc aat ccg ctg aca      624
Glu Leu Gly Leu His Leu Asn Thr Ala Tyr Leu Val Asn Pro Leu Thr
        195                 200                 205 gat cct cgc ctg gag gaa ttc gcc gaa caa ttc gcg gag ctg cgc aag      672
Asp Pro Arg Leu Glu Glu Phe Ala Glu Gln Phe Ala Glu Leu Arg Lys
    210                 215                 220 tca aag agc gtc act atc gat gaa gcc cgc gaa atc atg aag gat att      720
Ser Lys Ser Val Thr Ile Asp Glu Ala Arg Glu Ile Met Lys Asp Ile
225                 230                 235                 240 tcc tac ttc ggc acc atg atg gtc cac aac ggc gac gcc gac gga atg      768
Ser Tyr Phe Gly Thr Met Met Val His Asn Gly Asp Ala Asp Gly Met
                245                 250                 255 gta tcc ggt gca gca aac acc acc gca cac acc att aag cca agc ttc      816
Val Ser Gly Ala Ala Asn Thr Thr Ala His Thr Ile Lys Pro Ser Phe
            260                 265                 270 cag atc atc aaa act gtt cca gaa gca tcc gtc gtt tct tcc atc ttc      864
Gln Ile Ile Lys Thr Val Pro Glu Ala Ser Val Val Ser Ser Ile Phe
        275                 280                 285 ctc atg gtg ctg cgc ggg cga ctg tgg gca ttc ggc gac tgt gct gtt      912
Leu Met Val Leu Arg Gly Arg Leu Trp Ala Phe Gly Asp Cys Ala Val
    290                 295                 300 aac ccg aac cca act gct gaa cag ctt ggt gaa atc gcc gtt gtg tca      960
Asn Pro Asn Pro Thr Ala Glu Gln Leu Gly Glu Ile Ala Val Val Ser
305                 310                 315                 320 gca aaa act gca gca caa ttt ggc att gat cct cgc gta gcc atc ttg     1008
Ala Lys Thr Ala Ala Gln Phe Gly Ile Asp Pro Arg Val Ala Ile Leu
                325                 330                 335 tcc tac tcc act ggc aac tcc ggc gga ggc tca gat gtg gat cgc gcc     1056
Ser Tyr Ser Thr Gly Asn Ser Gly Gly Gly Ser Asp Val Asp Arg Ala
            340                 345                 350 atc gac gct ctt gca gaa gca cgc cga ctt aac cca gaa cta tgc gtc     1104
Ile Asp Ala Leu Ala Glu Ala Arg Arg Leu Asn Pro Glu Leu Cys Val
        355                 360                 365
```

```
                                                                    -continued gat gga cca ctt cag ttc gac gcc gcc gtc gac ccg ggt gtg gcg cgc    1152
Asp Gly Pro Leu Gln Phe Asp Ala Ala Val Asp Pro Gly Val Ala Arg
    370                 375                 380 aag aag atg cca gac tct gac gtc gct ggc cag gca aat gtg ttt atc    1200
Lys Lys Met Pro Asp Ser Asp Val Ala Gly Gln Ala Asn Val Phe Ile
385                 390                 395                 400 ttc cct gac ctg gaa gcc gga aac atc ggc tac aaa act gca caa cgc    1248
Phe Pro Asp Leu Glu Ala Gly Asn Ile Gly Tyr Lys Thr Ala Gln Arg
                405                 410                 415 acc ggt cac gcc ctg gca gtt ggt ccg att ctg cag ggc cta aac aaa    1296
Thr Gly His Ala Leu Ala Val Gly Pro Ile Leu Gln Gly Leu Asn Lys
            420                 425                 430 cca gtc aac gac ctt tcc cgt ggc gca aca gtc cct gac atc gtc aac    1344
Pro Val Asn Asp Leu Ser Arg Gly Ala Thr Val Pro Asp Ile Val Asn
        435                 440                 445 aca gta gcc atc aca gca att cag gca gga gga cgc agc ta  atg gca    1391
Thr Val Ala Ile Thr Ala Ile Gln Ala Gly Gly Arg Ser     Met Ala
    450                 455                 460 ttg gca ctt gtt ttg aac tcc ggt tca tct tcc atc aaa ttc cag ctg    1439
Leu Ala Leu Val Leu Asn Ser Gly Ser Ser Ser Ile Lys Phe Gln Leu
465                 470                 475 gtc aac ccc gaa aac tct gcc atc gac gag cca tat gtt tct ggt ctt    1487
Val Asn Pro Glu Asn Ser Ala Ile Asp Glu Pro Tyr Val Ser Gly Leu
480                 485                 490                 495 gtg gag cag att ggt gag cca aac ggc cgc atc gta ctc aaa ata gag    1535
Val Glu Gln Ile Gly Glu Pro Asn Gly Arg Ile Val Leu Lys Ile Glu
                500                 505                 510 ggt gaa aaa tat acc cta gag aca ccc atc gca gat cac tcc gaa ggc    1583
Gly Glu Lys Tyr Thr Leu Glu Thr Pro Ile Ala Asp His Ser Glu Gly
            515                 520                 525 cta aac ctg gcg ttc gat ctc atg gac cag cac aac tgt ggt cct tcc    1631
Leu Asn Leu Ala Phe Asp Leu Met Asp Gln His Asn Cys Gly Pro Ser
        530                 535                 540 caa ctg gaa atc acc gca gtt gga cac cgc gtg gtc cac ggc gga atc    1679
Gln Leu Glu Ile Thr Ala Val Gly His Arg Val Val His Gly Gly Ile
    545                 550                 555 ttg ttc tcc gca ccg gaa ctt atc act gat gaa atc gtg gaa atg atc    1727
Leu Phe Ser Ala Pro Glu Leu Ile Thr Asp Glu Ile Val Glu Met Ile
560                 565                 570                 575 cgc gat ctc att cca ctc gca cca ctg cac aac cct gca aac gtt gac    1775
Arg Asp Leu Ile Pro Leu Ala Pro Leu His Asn Pro Ala Asn Val Asp
                580                 585                 590 ggc att gat gtt gct cga aaa att ctc ccc gat gtc cca cac gta gct    1823
Gly Ile Asp Val Ala Arg Lys Ile Leu Pro Asp Val Pro His Val Ala
            595                 600                 605 gtc ttt gac acc ggt ttc ttc cac tca ctt cca cca gca gct gcg ctg    1871
Val Phe Asp Thr Gly Phe Phe His Ser Leu Pro Pro Ala Ala Ala Leu
        610                 615                 620 tat gcc atc aac aag gat gtc gca gct gaa cac gga atc agg cgc tat    1919
Tyr Ala Ile Asn Lys Asp Val Ala Ala Glu His Gly Ile Arg Arg Tyr
    625                 630                 635 ggt ttc cac ggc acc tcc cat gaa ttt gtg tcc aag cgc gtg gtg gaa    1967
Gly Phe His Gly Thr Ser His Glu Phe Val Ser Lys Arg Val Val Glu
640                 645                 650                 655 att ctg gaa aag ccc acc gaa gac atc aac acc atc acc ttc cac ctg    2015
Ile Leu Glu Lys Pro Thr Glu Asp Ile Asn Thr Ile Thr Phe His Leu
                660                 665                 670 ggc aac ggc gca tcc atg gct gct gtt caa ggt ggc cgt gcg gta gat    2063
Gly Asn Gly Ala Ser Met Ala Ala Val Gln Gly Gly Arg Ala Val Asp
            675                 680                 685
```

| | | | | | | | | | | | | | | | | |
|---|---|---|---|---|---|---|---|---|---|---|---|---|---|---|---|---|
| act | tcc | atg | ggt | atg | aca | cct | ctc | gcg | ggc | ctt | gtc | atg | ggt | acc | cga | 2111 |
| Thr | Ser | Met | Gly | Met | Thr | Pro | Leu | Ala | Gly | Leu | Val | Met | Gly | Thr | Arg | |
| | | 690 | | | | 695 | | | | 700 | | | | | | |
| agc | ggt | gac | att | gat | cca | ggt | atc | gtc | ttc | cac | ctt | tcc | cgc | acc | gct | 2159 |
| Ser | Gly | Asp | Ile | Asp | Pro | Gly | Ile | Val | Phe | His | Leu | Ser | Arg | Thr | Ala | |
| | 705 | | | | | 710 | | | | | 715 | | | | | |
| ggc | atg | agc | atc | gat | gag | atc | gat | aat | ctg | ctg | aac | aaa | aag | tcg | ggt | 2207 |
| Gly | Met | Ser | Ile | Asp | Glu | Ile | Asp | Asn | Leu | Leu | Asn | Lys | Lys | Ser | Gly | |
| 720 | | | | | 725 | | | | | 730 | | | | | 735 | |
| gta | aag | gga | ctt | tcc | ggt | gtt | aat | gat | ttc | cgt | gaa | ctg | cgg | gaa | atg | 2255 |
| Val | Lys | Gly | Leu | Ser | Gly | Val | Asn | Asp | Phe | Arg | Glu | Leu | Arg | Glu | Met | |
| | | | | 740 | | | | | 745 | | | | | 750 | | |
| atc | gac | aac | aat | gat | caa | gat | gcc | tgg | tcc | gcg | tac | aac | att | tac | ata | 2303 |
| Ile | Asp | Asn | Asn | Asp | Gln | Asp | Ala | Trp | Ser | Ala | Tyr | Asn | Ile | Tyr | Ile | |
| | | | 755 | | | | | 760 | | | | | 765 | | | |
| cac | caa | ctc | cgc | cgc | tac | ctc | ggt | tcc | tac | atg | gtg | gca | ctg | gga | cgg | 2351 |
| His | Gln | Leu | Arg | Arg | Tyr | Leu | Gly | Ser | Tyr | Met | Val | Ala | Leu | Gly | Arg | |
| | | | 770 | | | | | 775 | | | | | 780 | | | |
| gta | gac | acc | atc | gtg | ttc | acc | gcc | ggt | gtc | ggt | gaa | aat | gcc | cag | ttt | 2399 |
| Val | Asp | Thr | Ile | Val | Phe | Thr | Ala | Gly | Val | Gly | Glu | Asn | Ala | Gln | Phe | |
| | 785 | | | | | 790 | | | | | 795 | | | | | |
| gtc | cgt | gag | gat | gcc | ttg | gca | ggt | ttg | gaa | atg | tac | gga | att | gag | atc | 2447 |
| Val | Arg | Glu | Asp | Ala | Leu | Ala | Gly | Leu | Glu | Met | Tyr | Gly | Ile | Glu | Ile | |
| 800 | | | | | 805 | | | | | 810 | | | | | 815 | |
| gat | cca | gag | cgt | aac | gca | ttg | cca | aac | gat | ggt | cct | cga | ttg | att | tcc | 2495 |
| Asp | Pro | Glu | Arg | Asn | Ala | Leu | Pro | Asn | Asp | Gly | Pro | Arg | Leu | Ile | Ser | |
| | | | | 820 | | | | | 825 | | | | | 830 | | |
| acc | gat | gcc | tcc | aag | gtg | aag | gtg | ttt | gtt | att | cca | act | aat | gaa | gag | 2543 |
| Thr | Asp | Ala | Ser | Lys | Val | Lys | Val | Phe | Val | Ile | Pro | Thr | Asn | Glu | Glu | |
| | | | 835 | | | | | 840 | | | | | 845 | | | |
| tta | gct | atc | gct | agg | tac | gcg | gtg | aag | ttc | gct | tag | | | | | 2579 |
| Leu | Ala | Ile | Ala | Arg | Tyr | Ala | Val | Lys | Phe | Ala | | | | | | |
| | | 850 | | | | | 855 | | | | | | | | | |

<210> SEQ ID NO 8
<211> LENGTH: 461
<212> TYPE: PRT
<213> ORGANISM: Brevibacterium flavum

<400> SEQUENCE: 8

Met Ser Asp Thr Pro Thr Ser Ala Leu Ile Thr Thr Val Asn Arg Ser
1               5                   10                  15

Phe Asp Gly Phe Asp Leu Glu Glu Val Ala Ala Asp Leu Gly Val Arg
                20                  25                  30

Leu Thr Tyr Leu Pro Asp Glu Glu Leu Glu Val Ser Lys Val Leu Ala
            35                  40                  45

Ala Asp Leu Leu Ala Glu Gly Pro Ala Leu Ile Ile Gly Val Gly Asn
        50                  55                  60

Thr Phe Phe Asp Ala Gln Val Ala Ala Leu Gly Val Pro Val Leu
65                  70                  75                  80

Leu Leu Val Asp Lys Gln Gly Lys His Val Ala Leu Ala Arg Thr Gln
                85                  90                  95

Val Asn Asn Ala Gly Ala Val Val Ala Ala Phe Thr Ala Glu Gln
            100                 105                 110

Glu Pro Met Pro Asp Lys Leu Arg Lys Ala Val Arg Asn His Ser Asn
        115                 120                 125

Leu Glu Pro Val Met Ser Ala Glu Leu Phe Glu Asn Trp Leu Leu Lys
    130                 135                 140

```
Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
            165                 170                 175

Asp Ile Thr Ile Leu Gly Asp Pro Val Lys Ile Lys Glu Arg Ala Thr
        180                 185                 190

Glu Leu Gly Leu His Leu Asn Thr Ala Tyr Leu Val Asn Pro Leu Thr
    195                 200                 205

Asp Pro Arg Leu Glu Glu Phe Ala Glu Gln Phe Ala Glu Leu Arg Lys
210                 215                 220

Ser Lys Ser Val Thr Ile Asp Glu Ala Arg Glu Ile Met Lys Asp Ile
225                 230                 235                 240

Ser Tyr Phe Gly Thr Met Met Val His Asn Gly Asp Ala Asp Gly Met
            245                 250                 255

Val Ser Gly Ala Ala Asn Thr Thr Ala His Thr Ile Lys Pro Ser Phe
        260                 265                 270

Gln Ile Ile Lys Thr Val Pro Glu Ala Ser Val Val Ser Ser Ile Phe
    275                 280                 285

Leu Met Val Leu Arg Gly Arg Leu Trp Ala Phe Gly Asp Cys Ala Val
290                 295                 300

Asn Pro Asn Pro Thr Ala Glu Gln Leu Gly Glu Ile Ala Val Val Ser
305                 310                 315                 320

Ala Lys Thr Ala Ala Gln Phe Gly Ile Asp Pro Arg Val Ala Ile Leu
            325                 330                 335

Ser Tyr Ser Thr Gly Asn Ser Gly Gly Ser Asp Val Asp Arg Ala
        340                 345                 350

Ile Asp Ala Leu Ala Glu Ala Arg Arg Leu Asn Pro Glu Leu Cys Val
            355                 360                 365

Asp Gly Pro Leu Gln Phe Asp Ala Ala Val Asp Pro Gly Val Ala Arg
370                 375                 380

Lys Lys Met Pro Asp Ser Asp Val Ala Gly Gln Ala Asn Val Phe Ile
385                 390                 395                 400

Phe Pro Asp Leu Glu Ala Gly Asn Ile Gly Tyr Lys Thr Ala Gln Arg
                405                 410                 415

Thr Gly His Ala Leu Ala Val Gly Pro Ile Leu Gln Gly Leu Asn Lys
            420                 425                 430

Pro Val Asn Asp Leu Ser Arg Gly Ala Thr Val Pro Asp Ile Val Asn
        435                 440                 445

Thr Val Ala Ile Thr Ala Ile Gln Ala Gly Gly Arg Ser
    450                 455                 460

<210> SEQ ID NO 9
<211> LENGTH: 397
<212> TYPE: PRT
<213> ORGANISM: Brevibacterium flavum

<400> SEQUENCE: 9

Met Ala Leu Ala Leu Val Leu Asn Ser Gly Ser Ser Ile Lys Phe
1               5                   10                  15

Gln Leu Val Asn Pro Glu Asn Ser Ala Ile Asp Glu Pro Tyr Val Ser
            20                  25                  30

Gly Leu Val Glu Gln Ile Gly Glu Pro Asn Gly Arg Ile Val Leu Lys
        35                  40                  45

Ile Glu Gly Glu Lys Tyr Thr Leu Glu Thr Pro Ile Ala Asp His Ser
    50                  55                  60
```

```
Glu Gly Leu Asn Leu Ala Phe Asp Leu Met Asp Gln His Asn Cys Gly
 65                  70                  75                  80

Pro Ser Gln Leu Glu Ile Thr Ala Val Gly His Arg Val Val His Gly
                 85                  90                  95

Gly Ile Leu Phe Ser Ala Pro Glu Leu Ile Thr Asp Glu Ile Val Glu
            100                 105                 110

Met Ile Arg Asp Leu Ile Pro Leu Ala Pro Leu His Asn Pro Ala Asn
        115                 120                 125

Val Asp Gly Ile Asp Val Ala Arg Lys Ile Leu Pro Asp Val Pro His
130                 135                 140

Val Ala Val Phe Asp Thr Gly Phe Phe His Ser Leu Pro Pro Ala Ala
145                 150                 155                 160

Ala Leu Tyr Ala Ile Asn Lys Asp Val Ala Ala Glu His Gly Ile Arg
                165                 170                 175

Arg Tyr Gly Phe His Gly Thr Ser His Glu Phe Val Ser Lys Arg Val
            180                 185                 190

Val Glu Ile Leu Glu Lys Pro Thr Glu Asp Ile Asn Thr Ile Thr Phe
        195                 200                 205

His Leu Gly Asn Gly Ala Ser Met Ala Ala Val Gln Gly Gly Arg Ala
210                 215                 220

Val Asp Thr Ser Met Gly Met Thr Pro Leu Ala Gly Leu Val Met Gly
225                 230                 235                 240

Thr Arg Ser Gly Asp Ile Asp Pro Gly Ile Val Phe His Leu Ser Arg
                245                 250                 255

Thr Ala Gly Met Ser Ile Asp Glu Ile Asp Asn Leu Leu Asn Lys Lys
            260                 265                 270

Ser Gly Val Lys Gly Leu Ser Gly Val Asn Asp Phe Arg Glu Leu Arg
        275                 280                 285

Glu Met Ile Asp Asn Asn Asp Gln Asp Ala Trp Ser Ala Tyr Asn Ile
290                 295                 300

Tyr Ile His Gln Leu Arg Arg Tyr Leu Gly Ser Tyr Met Val Ala Leu
305                 310                 315                 320

Gly Arg Val Asp Thr Ile Val Phe Thr Ala Gly Val Gly Glu Asn Ala
                325                 330                 335

Gln Phe Val Arg Glu Asp Ala Leu Ala Gly Leu Glu Met Tyr Gly Ile
            340                 345                 350

Glu Ile Asp Pro Glu Arg Asn Ala Leu Pro Asn Asp Gly Pro Arg Leu
        355                 360                 365

Ile Ser Thr Asp Ala Ser Lys Val Lys Val Phe Val Ile Pro Thr Asn
370                 375                 380

Glu Glu Leu Ala Ile Ala Arg Tyr Ala Val Lys Phe Ala
385                 390                 395

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgggagcac aggatgacgc ctaac                                          25

<210> SEQ ID NO 11
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 11
tccccagctc tctaacgctt gag                                            23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcacgacagg tttcccgact g                                              21

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acaacactca accctatctc ggtcta                                         26

<210> SEQ ID NO 14
<211> LENGTH: 3600
<212> TYPE: DNA
<213> ORGANISM: Corynebacterium glutamicum
<220> FEATURE:
<221> NAME/KEY: CDS
<222> LOCATION: (1037)..(2545)

<400> SEQUENCE: 14
gaagcgctac ggacttcgcg ccggcgtcga cagcaatgcg tccagcatcc aagtgagtat     60
ggtgctcatc atcaatacca acgcggaact tcaccgtcac cggaatgtcc gtgccttccg    120
tagccttcac agccgcggaa acgatgtttt caaacaaacg gcgcttgtaa ggaatcgcag    180
aaccgccacc ccggcgcgtg acctttggaa ccgggcagcc aaagttcata tcaatatgat    240
ccgccaagtt ttcatcaacg atcatcttcg ccgcttcgta ggtgtacttc gggtcaaccg    300
tgtacagctg caagcttcgg ggattttcat ccggcgcgaa ggtggtcatg tgcatggttt    360
tctcattgcg ctcaacaaga gcacgcgcag tcaccatttc acagacgtac agccccgaga    420
ttgttcccgt gcgttgcatt tcctgttcac ggcacagcgt gcggaaagca acgttggtta    480
caccagccat gggggctaga accacagggg aggcaaggtc aaaggggccg attttttaaag   540 tcacctaact attgtccccc gtgaatcagg ttgggcaaaa tatttgaagc aaattgtgag    600
cagggcgcaa ctaggaaagt ggtgtgcttt cacttttttgg gggctggggt tgggttaagc   660
ttcgcgggct ctagggttgg tctgagcttt attcctgggc tttgggaggc ttgcaaacag    720
ggggcatgca aatttggggg taatgctggg ccttgaaatc ccactatcac agatagtatt    780
cgggcatttc ctgtcacgat ggtttatcct tgggacacaa catcaaagtg gggtacatca    840
tatgcttccg gttgaagtga cctatctgaa aagattggtc gaaccttgaa gcaatggtgt    900
gaactgcgtt aacgaatttt gtcggacgtt aaaatggtcg cattctgctt gctgaagtgg    960
cacacctatg tgttctgctt gggtatagca gtgcgggaaa aatttgaaaa agtccgatta   1020
```

```
                                                            -continued cctgaggagg tattca atg tct gat cgc att gct tca gaa aag ctg cgc tcc          1072
                Met Ser Asp Arg Ile Ala Ser Glu Lys Leu Arg Ser
                 1               5                  10 aag ctc atg tcc gcc gac gag gcg gca cag ttt gtt aac cac ggt gac            1120
Lys Leu Met Ser Ala Asp Glu Ala Ala Gln Phe Val Asn His Gly Asp
         15                  20                  25 aag gtt ggt ttc tcc ggc ttc acc ggc gct ggc tac cca aag gca ctg            1168
Lys Val Gly Phe Ser Gly Phe Thr Gly Ala Gly Tyr Pro Lys Ala Leu
     30                  35                  40 cct acg gca atc gct aac cgg gct aaa gaa gca cac ggt gca ggc aac            1216
Pro Thr Ala Ile Ala Asn Arg Ala Lys Glu Ala His Gly Ala Gly Asn
45                  50                  55                  60 gac tac gca atc gac ctg ttc act ggc gca tcg acc gcc cct gac tgc            1264
Asp Tyr Ala Ile Asp Leu Phe Thr Gly Ala Ser Thr Ala Pro Asp Cys
                 65                  70                  75 gat ggc gta ctt gca gaa gct gac gct atc cgc tgg cgc atg cca tac            1312
Asp Gly Val Leu Ala Glu Ala Asp Ala Ile Arg Trp Arg Met Pro Tyr
         80                  85                  90 gca tct gat cca atc atg cgt aac aag atc aac tcc ggc tcc atg gga            1360
Ala Ser Asp Pro Ile Met Arg Asn Lys Ile Asn Ser Gly Ser Met Gly
     95                 100                 105 tac tcc gat atc cac ctg tcc cac tcc ggc cag cag gtt gaa gag ggc            1408
Tyr Ser Asp Ile His Leu Ser His Ser Gly Gln Gln Val Glu Glu Gly
110                 115                 120 ttc ttc ggc cag ctc aac gta gct gtc att gaa atc acc cgc atc act            1456
Phe Phe Gly Gln Leu Asn Val Ala Val Ile Glu Ile Thr Arg Ile Thr
125                 130                 135                 140 gaa gag ggc tac atc atc cct tct tcc tcc gtg ggt aac aac gtt gag            1504
Glu Glu Gly Tyr Ile Ile Pro Ser Ser Ser Val Gly Asn Asn Val Glu
                145                 150                 155 tgg ctc aac gct gca gag aag gtc atc ctc gag gtt aac tct tgg cag            1552
Trp Leu Asn Ala Ala Glu Lys Val Ile Leu Glu Val Asn Ser Trp Gln
        160                 165                 170 tct gaa gac ctc gaa ggt atg cac gac atc tgg tct gtt cct gcc ctg            1600
Ser Glu Asp Leu Glu Gly Met His Asp Ile Trp Ser Val Pro Ala Leu
    175                 180                 185 cca aac cgc att gcc gtg cca atc aac aag cca ggc gac cgc atc ggt            1648
Pro Asn Arg Ile Ala Val Pro Ile Asn Lys Pro Gly Asp Arg Ile Gly
190                 195                 200 aag acc tac atc gag ttc gac acc gac aag gtt gtt gct gtt gtt gag            1696
Lys Thr Tyr Ile Glu Phe Asp Thr Asp Lys Val Val Ala Val Val Glu
205                 210                 215                 220 acc aac acc gca gac cgc aac gca cca ttc aag cct gtc gac gac atc            1744
Thr Asn Thr Ala Asp Arg Asn Ala Pro Phe Lys Pro Val Asp Asp Ile
                225                 230                 235 tct aag aag atc gct ggc aac ttc ctc gac ttc ctg gaa agc gaa gtt            1792
Ser Lys Lys Ile Ala Gly Asn Phe Leu Asp Phe Leu Glu Ser Glu Val
        240                 245                 250 gct gca ggt cgc ctg tcc tac gac ggc tac atc atg cag tcc ggc gtg            1840
Ala Ala Gly Arg Leu Ser Tyr Asp Gly Tyr Ile Met Gln Ser Gly Val
    255                 260                 265 ggc aac gtg cca aac gcg gtg atg gca ggc ctg ctg gaa tcc aag ttt            1888
Gly Asn Val Pro Asn Ala Val Met Ala Gly Leu Leu Glu Ser Lys Phe
270                 275                 280 gag aac atc cag gcc tac acc gaa gtt atc cag gac ggc atg gtg gac            1936
Glu Asn Ile Gln Ala Tyr Thr Glu Val Ile Gln Asp Gly Met Val Asp
285                 290                 295                 300 ctc atc gac gcc ggc aag atg acc gtt gca tcc gca act tcc ttc tcc            1984
Leu Ile Asp Ala Gly Lys Met Thr Val Ala Ser Ala Thr Ser Phe Ser
                305                 310                 315
```

```
ctg tct cct gag tac gca gag aag atg aac aac gag gct aag cgt tac      2032
Leu Ser Pro Glu Tyr Ala Glu Lys Met Asn Asn Glu Ala Lys Arg Tyr
            320                 325                 330 cgc gag tcc att atc ctg cgc cca cag cag atc tct aac cac cca gag      2080
Arg Glu Ser Ile Ile Leu Arg Pro Gln Gln Ile Ser Asn His Pro Glu
        335                 340                 345 gtc atc cgc cgc gtt ggc ctg atc gcc acc aac ggt ctc atc gag gct      2128
Val Ile Arg Arg Val Gly Leu Ile Ala Thr Asn Gly Leu Ile Glu Ala
    350                 355                 360 gac att tac ggc aac gtc aac tcc acc aac gtt tct ggc tcc cgc gtc      2176
Asp Ile Tyr Gly Asn Val Asn Ser Thr Asn Val Ser Gly Ser Arg Val
365                 370                 375                 380 atg aac ggc atc ggc ggc tcc ggc gac ttc acc cgt aac ggc tac atc      2224
Met Asn Gly Ile Gly Gly Ser Gly Asp Phe Thr Arg Asn Gly Tyr Ile
                385                 390                 395 tcc agc ttc atc acc cct tca gag gca aag ggc ggc gca atc tct gcg      2272
Ser Ser Phe Ile Thr Pro Ser Glu Ala Lys Gly Gly Ala Ile Ser Ala
            400                 405                 410 atc gtt cct ttc gca tcc cac atc gac cac acc gag cac gat gtc atg      2320
Ile Val Pro Phe Ala Ser His Ile Asp His Thr Glu His Asp Val Met
        415                 420                 425 gtt gtt atc tct gag tac ggt tac gca gac ctt cgt ggt ctg gct cca      2368
Val Val Ile Ser Glu Tyr Gly Tyr Ala Asp Leu Arg Gly Leu Ala Pro
    430                 435                 440 cgt gag cgc gtt gcc aag atg atc ggc ctg gct cac cct gat tac cgc      2416
Arg Glu Arg Val Ala Lys Met Ile Gly Leu Ala His Pro Asp Tyr Arg
445                 450                 455                 460 cca ctg ctc gag gag tac tac gct cgc gca acc tcc ggt gac aac aag      2464
Pro Leu Leu Glu Glu Tyr Tyr Ala Arg Ala Thr Ser Gly Asp Asn Lys
                465                 470                 475 tac atg cag acc cct cat gat ctt gca acc gcg ttt gat ttc cac atc      2512
Tyr Met Gln Thr Pro His Asp Leu Ala Thr Ala Phe Asp Phe His Ile
            480                 485                 490 aac ctg gct aag aac ggc tcc atg aag gca taa gttttttctt ggtttagaaa    2565
Asn Leu Ala Lys Asn Gly Ser Met Lys Ala
        495                 500 ccgccgcctc gacaacattt cgaggcggcg gtttctttta ttacctgggt tttgagcgtt   2625
aaattagacc aggtcaggct agtgtttggt agctaattga gggcgatttt aataaggccg   2685
gtgccatgta ctaatatggt ctgagttggg cctatagctc agttggtaga gctacggact   2745
tttaatccgc aggtcttggg ttcgagtccc aatgggccca catcttaagt accctgtttt   2805
tggagaatgc tccgagccag gggtactttt cttttcctca cacacagtag ctgctgagaa   2865
aaatgaagac cttttgttag gttgggagta tgaccaaccc atacgaggcc ttcataccgc   2925
tcaagcatcg tacggggatt gaacccgagc acacctttg ggaatgggaa acaaaaggg    2985 ttcacattgc aaggagacgt cgagaagcgc ccgtccgcgt tatcgtggtg catgggctag   3045
gcacccatag tggcgccctc tggccccctcg tcgcggccat tgaggcgcg acctcgccg    3105 cgatcgacct gcctaaaact ccgctttacg acgattggct gcgccttttta gaatctttca  3165 tctcttccga agacgacggt cggccactca tcctgatcgg tgcaggcacc ggaggcttgc   3225
tttgcgcaga agctgcacac cgcacaggac tggtcgcaca cgtcattgcc acctgcctgc   3285 tcaaccctc cgaccagccg acgcgccggg cactgttcag gttttcaccg ctgactcggt    3345
tgatccaagg ccgcttgcgc aaccgcgaaa ttcccgtgac cagagtgttg aacttcagca   3405
aaatcagccg cagcccagcc ctgagcaaat tgtgcgcggc cgatgaattt agcggagcat   3465
ccaaaataac ctggggtttc ctcgcgtcat atgtgcaaca caaggccaaa ctgggtgcag   3525
```

```
ttcccgtcac tctgatgcac cctgaccacg accttctgac tcccgttgag ctcagtctgc    3585
gtacgctttc gcgcc                                                     3600
```

<210> SEQ ID NO 15
<211> LENGTH: 502
<212> TYPE: PRT
<213> ORGANISM: Corynebacterium glutamicum

<400> SEQUENCE: 15

```
Met Ser Asp Arg Ile Ala Ser Glu Lys Leu Arg Ser Lys Leu Met Ser
1               5                   10                  15

Ala Asp Glu Ala Ala Gln Phe Val Asn His Gly Asp Lys Val Gly Phe
            20                  25                  30

Ser Gly Phe Thr Gly Ala Gly Tyr Pro Lys Ala Leu Pro Thr Ala Ile
        35                  40                  45

Ala Asn Arg Ala Lys Glu Ala His Gly Ala Gly Asn Asp Tyr Ala Ile
    50                  55                  60

Asp Leu Phe Thr Gly Ala Ser Thr Ala Pro Asp Cys Asp Gly Val Leu
65                  70                  75                  80

Ala Glu Ala Asp Ala Ile Arg Trp Arg Met Pro Tyr Ala Ser Asp Pro
                85                  90                  95

Ile Met Arg Asn Lys Ile Asn Ser Gly Ser Met Gly Tyr Ser Asp Ile
            100                 105                 110

His Leu Ser His Ser Gly Gln Gln Val Glu Glu Gly Phe Phe Gly Gln
        115                 120                 125

Leu Asn Val Ala Val Ile Glu Ile Thr Arg Ile Thr Glu Glu Gly Tyr
    130                 135                 140

Ile Ile Pro Ser Ser Val Gly Asn Asn Val Glu Trp Leu Asn Ala
145                 150                 155                 160

Ala Glu Lys Val Ile Leu Glu Val Asn Ser Trp Gln Ser Glu Asp Leu
                165                 170                 175

Glu Gly Met His Asp Ile Trp Ser Val Pro Ala Leu Pro Asn Arg Ile
            180                 185                 190

Ala Val Pro Ile Asn Lys Pro Gly Asp Arg Ile Gly Lys Thr Tyr Ile
        195                 200                 205

Glu Phe Asp Thr Asp Lys Val Val Ala Val Glu Thr Asn Thr Ala
    210                 215                 220

Asp Arg Asn Ala Pro Phe Lys Pro Val Asp Asp Ile Ser Lys Lys Ile
225                 230                 235                 240

Ala Gly Asn Phe Leu Asp Phe Leu Glu Ser Glu Val Ala Ala Gly Arg
                245                 250                 255

Leu Ser Tyr Asp Gly Tyr Ile Met Gln Ser Gly Val Gly Asn Val Pro
            260                 265                 270

Asn Ala Val Met Ala Gly Leu Leu Glu Ser Lys Phe Glu Asn Ile Gln
        275                 280                 285

Ala Tyr Thr Glu Val Ile Gln Asp Gly Met Val Asp Leu Ile Asp Ala
    290                 295                 300

Gly Lys Met Thr Val Ala Ser Ala Thr Ser Phe Ser Leu Ser Pro Glu
305                 310                 315                 320

Tyr Ala Glu Lys Met Asn Asn Glu Ala Lys Arg Tyr Arg Glu Ser Ile
                325                 330                 335

Ile Leu Arg Pro Gln Gln Ile Ser Asn His Pro Glu Val Ile Arg Arg
            340                 345                 350

Val Gly Leu Ile Ala Thr Asn Gly Leu Ile Glu Ala Asp Ile Tyr Gly
        355                 360                 365
```

```
Asn Val Asn Ser Thr Asn Val Ser Gly Ser Arg Val Met Asn Gly Ile
    370                 375                 380
Gly Gly Ser Gly Asp Phe Thr Arg Asn Gly Tyr Ile Ser Ser Phe Ile
385                 390                 395                 400
Thr Pro Ser Glu Ala Lys Gly Gly Ala Ile Ser Ala Ile Val Pro Phe
                405                 410                 415
Ala Ser His Ile Asp His Thr Glu His Asp Val Met Val Ile Ser
                420                 425                 430
Glu Tyr Gly Tyr Ala Asp Leu Arg Gly Leu Ala Pro Arg Glu Arg Val
            435                 440                 445
Ala Lys Met Ile Gly Leu Ala His Pro Asp Tyr Arg Pro Leu Leu Glu
        450                 455                 460
Glu Tyr Tyr Ala Arg Ala Thr Ser Gly Asp Asn Lys Tyr Met Gln Thr
465                 470                 475                 480
Pro His Asp Leu Ala Thr Ala Phe Asp Phe His Ile Asn Leu Ala Lys
                485                 490                 495
Asn Gly Ser Met Lys Ala
            500

<210> SEQ ID NO 16
<211> LENGTH: 3780
<212> TYPE: DNA
<213> ORGANISM: Corynebacterium glutamicum
<220> FEATURE:
<221> NAME/KEY: CDS
<222> LOCATION: (996)..(2735)

<400> SEQUENCE: 16
taatgaggaa aaccgaaccc caccagaaga attccaacag cgcaccacca atgatcgggc      60
ctgccgcagc gccaagaatt gccacggaac cccaaatacc aattgcagtg ttgcgctcac     120
gctcatcctc aaacgtaatg cggatcgag ccaaggttgc aggcatcatc gttgccgcac      180
cgatgccaag gaaagctctc gcagcaacaa gagcccacgc agttggagca acgcagcac     240 caagtgaagc gattccgaaa atgctcaagc ccatgaggaa catccggcgg tggccgattt     300
tgtcacccaa agtgccggta cccaaaagaa ggcccgccat gagcagggga tatgcgttga     360
tgatccacaa cgcttgggtt tcggtggctg cgagctgttc acgcagcaga gggagtgcgg     420
tgtagagaat cgagttgtct acaccgatca gaaagagacc accgctgata acggcgagga     480
aagcccaacg ttgggttttc gtaggcgctt gcgcctgtaa ggtttctgaa gtcatggatc     540
gtaactgtaa cgaatggtcg gtacagttac aactcttttg ttggtgtttt agaccacggc     600
gctgtgtggc gatttaagac gtcggaaatc gtaggggact gtcagcgtgg gtcgggttct     660
ttgaggcgct tagaggcgat tctgtgaggt cacttttgt ggggtcgggg tctaaatttg      720
gccagttttc gaggcgacca gacaggcgtg cccacgatgt ttaaataggc gatcggtggg     780
catctgtgtt tggtttcgac gggctgaaac caaaccagac tgcccagcaa cgacggaaat     840
cccaaaagtg ggcatccctg tttggtaccg agtaccacc cgggcctgaa actccctggc     900
aggcgggcga agcgtggcaa caactggaat ttaagagcac aattgaagtc gcaccaagtt     960
aggcaacaca atagccataa cgttgaggag ttcag atg gca cac agc tac gca     1013
                                     Met Ala His Ser Tyr Ala
                                      1               5 gaa caa tta att gac act ttg gaa gct caa ggt gtg aag cga att tat     1061
Glu Gln Leu Ile Asp Thr Leu Glu Ala Gln Gly Val Lys Arg Ile Tyr
         10                  15                  20 ggt ttg gtg ggt gac agc ctt aat ccg atc gtg gat gct gtc cgc caa     1109
```

```
                  Gly Leu Val Gly Asp Ser Leu Asn Pro Ile Val Asp Ala Val Arg Gln
                               25                  30                  35 tca gat att gag tgg gtg cac gtt cga aat gag gaa gcg gcg gcg ttt                    1157
Ser Asp Ile Glu Trp Val His Val Arg Asn Glu Glu Ala Ala Ala Phe
     40                  45                  50 gca gcc ggt gcg gaa tcg ttg atc act ggg gag ctg gca gta tgt gct                    1205
Ala Ala Gly Ala Glu Ser Leu Ile Thr Gly Glu Leu Ala Val Cys Ala
 55                  60                  65                  70 gct tct tgt ggt cct gga aac aca cac ctg att cag ggt ctt tat gat                    1253
Ala Ser Cys Gly Pro Gly Asn Thr His Leu Ile Gln Gly Leu Tyr Asp
                 75                  80                  85 tcg cat cga aat ggt gcg aag gtg ttg gcc atc gct agc cat att ccg                    1301
Ser His Arg Asn Gly Ala Lys Val Leu Ala Ile Ala Ser His Ile Pro
         90                  95                 100 agt gcc cag att ggt tcg acg ttc ttc cag gaa acg cat ccg gag att                    1349
Ser Ala Gln Ile Gly Ser Thr Phe Phe Gln Glu Thr His Pro Glu Ile
            105                 110                 115 ttg ttt aag gaa tgc tct ggt tac tgc gag atg gtg aat ggt ggt gag                    1397
Leu Phe Lys Glu Cys Ser Gly Tyr Cys Glu Met Val Asn Gly Gly Glu
120                 125                 130 cag ggt gaa cgc att ttg cat cac gcg att cag tcc acc atg gcg ggt                    1445
Gln Gly Glu Arg Ile Leu His His Ala Ile Gln Ser Thr Met Ala Gly
135                 140                 145                 150 aaa ggt gtg tcg gtg gta gtg att cct ggt gat atc gct aag gaa gac                    1493
Lys Gly Val Ser Val Val Val Ile Pro Gly Asp Ile Ala Lys Glu Asp
                155                 160                 165 gca ggt gac ggt act tat tcc aat tcc act att tct tct ggc act cct                    1541
Ala Gly Asp Gly Thr Tyr Ser Asn Ser Thr Ile Ser Ser Gly Thr Pro
            170                 175                 180 gtg gtg ttc ccg gat cct act gag gct gca gcg ctg gtg gag gcg att                    1589
Val Val Phe Pro Asp Pro Thr Glu Ala Ala Ala Leu Val Glu Ala Ile
        185                 190                 195 aac aac gct aag tct gtc act ttg ttc tgc ggt gcg ggc gtg aag aat                    1637
Asn Asn Ala Lys Ser Val Thr Leu Phe Cys Gly Ala Gly Val Lys Asn
200                 205                 210 gct cgc gcg cag gtg ttg gag ttg gcg gag aag att aaa tca ccg atc                    1685
Ala Arg Ala Gln Val Leu Glu Leu Ala Glu Lys Ile Lys Ser Pro Ile
215                 220                 225                 230 ggg cat gcg ctg ggt ggt aag cag tac atc cag cat gag aat ccg ttt                    1733
Gly His Ala Leu Gly Gly Lys Gln Tyr Ile Gln His Glu Asn Pro Phe
                235                 240                 245 gag gtc ggc atg tct ggc ctg ctt ggt tac ggc gcc tgc gtg gat gcg                    1781
Glu Val Gly Met Ser Gly Leu Leu Gly Tyr Gly Ala Cys Val Asp Ala
            250                 255                 260 tcc aat gag gcg gat ctg ctg att cta ttg ggt acg gat ttc cct tat                    1829
Ser Asn Glu Ala Asp Leu Leu Ile Leu Leu Gly Thr Asp Phe Pro Tyr
        265                 270                 275 tct gat ttc ctt cct aaa gac aac gtt gcc cag gtg gat atc aac ggt                    1877
Ser Asp Phe Leu Pro Lys Asp Asn Val Ala Gln Val Asp Ile Asn Gly
280                 285                 290 gcg cac att ggt cga cgt acc acg gtg aag tat ccg gtg acc ggt gat                    1925
Ala His Ile Gly Arg Arg Thr Thr Val Lys Tyr Pro Val Thr Gly Asp
295                 300                 305                 310 gtt gct gca aca atc gaa aat att ttg cct cat gtg aag gaa aaa aca                    1973
Val Ala Ala Thr Ile Glu Asn Ile Leu Pro His Val Lys Glu Lys Thr
                315                 320                 325 gat cgt tcc ttc ctt gat cgg atg ctc aag gca cac gag cgt aag ttg                    2021
Asp Arg Ser Phe Leu Asp Arg Met Leu Lys Ala His Glu Arg Lys Leu
            330                 335                 340 agc tcg gtg gta gag acg tac aca cat aac gtc gag aag cat gtg cct                    2069
```

```
Ser Ser Val Val Glu Thr Tyr Thr His Asn Val Glu Lys His Val Pro
        345                 350                 355 att cac cct gaa tac gtt gcc tct att ttg aac gag ctg gcg gat aag      2117
Ile His Pro Glu Tyr Val Ala Ser Ile Leu Asn Glu Leu Ala Asp Lys
360                 365                 370 gat gcg gtg ttt act gtg gat acc ggc atg tgc aat gtg tgg cat gcg      2165
Asp Ala Val Phe Thr Val Asp Thr Gly Met Cys Asn Val Trp His Ala
375                 380                 385                 390 agg tac atc gag aat ccg gag gga acg cgc gac ttt gtg ggt tca ttc      2213
Arg Tyr Ile Glu Asn Pro Glu Gly Thr Arg Asp Phe Val Gly Ser Phe
                395                 400                 405 cgc cac ggc acg atg gct aat gcg ttg cct cat gcg att ggt gcg caa      2261
Arg His Gly Thr Met Ala Asn Ala Leu Pro His Ala Ile Gly Ala Gln
410                 415                 420 agt gtt gat cga aac cgc cag gtg atc gcg atg tgt ggc gat ggt ggt      2309
Ser Val Asp Arg Asn Arg Gln Val Ile Ala Met Cys Gly Asp Gly Gly
        425                 430                 435 ttg ggc atg ctg ctg ggt gag ctt ctg acc gtt aag ctg cac caa ctt      2357
Leu Gly Met Leu Leu Gly Glu Leu Leu Thr Val Lys Leu His Gln Leu
440                 445                 450 ccg ctg aag gct gtg gtg ttt aac aac agt tct ttg ggc atg gtg aag      2405
Pro Leu Lys Ala Val Val Phe Asn Asn Ser Ser Leu Gly Met Val Lys
455                 460                 465                 470 ttg gag atg ctc gtg gag gga cag cca gaa ttt ggt act gac cat gag      2453
Leu Glu Met Leu Val Glu Gly Gln Pro Glu Phe Gly Thr Asp His Glu
                475                 480                 485 gaa gtg aat ttc gca gag att gcg gcg gct gcg ggt atc aaa tcg gta      2501
Glu Val Asn Phe Ala Glu Ile Ala Ala Ala Ala Gly Ile Lys Ser Val
            490                 495                 500 cgc atc acc gat ccg aag aaa gtt cgc gag cag cta gct gag gca ttg      2549
Arg Ile Thr Asp Pro Lys Lys Val Arg Glu Gln Leu Ala Glu Ala Leu
        505                 510                 515 gca tat cct gga cct gta ctg atc gat atc gtc acg gat cct aat gcg      2597
Ala Tyr Pro Gly Pro Val Leu Ile Asp Ile Val Thr Asp Pro Asn Ala
520                 525                 530 ctg tcg atc cca cca acc atc acg tgg gaa cag gtc atg gga ttc agc      2645
Leu Ser Ile Pro Pro Thr Ile Thr Trp Glu Gln Val Met Gly Phe Ser
535                 540                 545                 550 aag gcg gcc acc cga acc gtc ttt ggt gga gga gta gga gcg atg atc      2693
Lys Ala Ala Thr Arg Thr Val Phe Gly Gly Gly Val Gly Ala Met Ile
                555                 560                 565 gat ctg gcc cgt tcg aac ata agg aat att cct act cca tga              2735
Asp Leu Ala Arg Ser Asn Ile Arg Asn Ile Pro Thr Pro
                570                 575 tgattgatac acctgctgtt ctcattgacc gcgagcgctt aactgccaac atttccagga    2795
tggcagctca cgccggtgcc catgagattg ccctgcgtcc gcatgtgaaa acgcacaaaa    2855
tcattgaaat tgcgcagatg caggtcgacg ccggtgcccg agggatcacc tgcgcaacca    2915
ttggcgaggc ggaaattttt gccggcgcag gttttacgga catctttatt gcatatccgc    2975
tgtatctaac cgatcatgca gtgcaacgcc tgaacgcgat ccccggagaa atttccattg    3035
gcgtggattc ggtagagatg gcacaggcga cggcgggttt gcgggaagat atcaaggctc    3095
tgattgaagt ggattcggga catcgtagaa gtggagtcac ggcgactgct tcagaattga    3155
gtcagatccg cgaggcgctg ggcagcaggt atgcaggagt gtttactttt cctgggcatt    3215
cttatggccc gggaaatggt gagcaggcag cagctgatga gcttcaggct ctaaacaaca    3275
gcgtccagcg acttgctggc ggcctgactt ctggcggttc ctcgccgtct gcgcagttta    3335
cagacgcaat cgatgagatg cgaccaggcg tgtatgtgtt taacgattcc cagcagatca    3395
```

```
cctcgggagc atgcactgag aagcaggtgg caatgacggt gctgtctact gtggtcagcc    3455
gaaatgtgtc agatcgtcgg atcattttgg atgcgggatc caaaatcctc agcactgata    3515
aaccagcatg gattgatggc aatggttttg ttctggggaa tcctgaagcc cgaatctctg    3575
ctttgtcgga gcatcacgca accattttct ggccagataa agtgctactt ccagtaatcg    3635
gggagcagct caacatcgtg cccaaccatg cctgcaacgt gattaatttg gtggatgagg    3695
tctacgttcg ggaagccgat ggcactttcc gtacctggaa ggtagttgcc cgcggcagaa    3755
acaattaggg aaacctcttg acctt                                          3780

<210> SEQ ID NO 17
<211> LENGTH: 579
<212> TYPE: PRT
<213> ORGANISM: Corynebacterium glutamicum

<400> SEQUENCE: 17

Met Ala His Ser Tyr Ala Glu Gln Leu Ile Asp Thr Leu Glu Ala Gln
1               5                   10                  15

Gly Val Lys Arg Ile Tyr Gly Leu Val Gly Asp Ser Leu Asn Pro Ile
            20                  25                  30

Val Asp Ala Val Arg Gln Ser Asp Ile Glu Trp Val His Val Arg Asn
        35                  40                  45

Glu Glu Ala Ala Ala Phe Ala Ala Gly Ala Glu Ser Leu Ile Thr Gly
    50                  55                  60

Glu Leu Ala Val Cys Ala Ala Ser Cys Gly Pro Gly Asn Thr His Leu
65                  70                  75                  80

Ile Gln Gly Leu Tyr Asp Ser His Arg Asn Gly Ala Lys Val Leu Ala
                85                  90                  95

Ile Ala Ser His Ile Pro Ser Ala Gln Ile Gly Ser Thr Phe Phe Gln
            100                 105                 110

Glu Thr His Pro Glu Ile Leu Phe Lys Glu Cys Ser Gly Tyr Cys Glu
        115                 120                 125

Met Val Asn Gly Gly Glu Gln Gly Glu Arg Ile Leu His His Ala Ile
    130                 135                 140

Gln Ser Thr Met Ala Gly Lys Gly Val Ser Val Val Ile Pro Gly
145                 150                 155                 160

Asp Ile Ala Lys Glu Asp Ala Gly Asp Gly Thr Tyr Ser Asn Ser Thr
                165                 170                 175

Ile Ser Ser Gly Thr Pro Val Val Phe Pro Asp Pro Thr Glu Ala Ala
            180                 185                 190

Ala Leu Val Glu Ala Ile Asn Asn Ala Lys Ser Val Thr Leu Phe Cys
        195                 200                 205

Gly Ala Gly Val Lys Asn Ala Arg Ala Gln Val Leu Glu Leu Ala Glu
    210                 215                 220

Lys Ile Lys Ser Pro Ile Gly His Ala Leu Gly Gly Lys Gln Tyr Ile
225                 230                 235                 240

Gln His Glu Asn Pro Phe Glu Val Gly Met Ser Gly Leu Leu Gly Tyr
                245                 250                 255

Gly Ala Cys Val Asp Ala Ser Asn Glu Ala Asp Leu Leu Ile Leu Leu
            260                 265                 270

Gly Thr Asp Phe Pro Tyr Ser Asp Phe Leu Pro Lys Asp Asn Val Ala
        275                 280                 285

Gln Val Asp Ile Asn Gly Ala His Ile Gly Arg Arg Thr Thr Val Lys
    290                 295                 300
```

```
Tyr Pro Val Thr Gly Asp Val Ala Ala Thr Ile Glu Asn Ile Leu Pro
305                 310                 315                 320

His Val Lys Glu Lys Thr Asp Arg Ser Phe Leu Asp Arg Met Leu Lys
                325                 330                 335

Ala His Glu Arg Lys Leu Ser Ser Val Val Glu Thr Tyr Thr His Asn
            340                 345                 350

Val Glu Lys His Val Pro Ile His Pro Glu Tyr Val Ala Ser Ile Leu
        355                 360                 365

Asn Glu Leu Ala Asp Lys Asp Ala Val Phe Thr Val Asp Thr Gly Met
    370                 375                 380

Cys Asn Val Trp His Ala Arg Tyr Ile Glu Asn Pro Glu Gly Thr Arg
385                 390                 395                 400

Asp Phe Val Gly Ser Phe Arg His Gly Thr Met Ala Asn Ala Leu Pro
                405                 410                 415

His Ala Ile Gly Ala Gln Ser Val Asp Arg Asn Arg Gln Val Ile Ala
            420                 425                 430

Met Cys Gly Asp Gly Gly Leu Gly Met Leu Leu Gly Glu Leu Leu Thr
            435                 440                 445

Val Lys Leu His Gln Leu Pro Leu Lys Ala Val Val Phe Asn Asn Ser
450                 455                 460

Ser Leu Gly Met Val Lys Leu Glu Met Leu Val Glu Gly Gln Pro Glu
465                 470                 475                 480

Phe Gly Thr Asp His Glu Val Asn Phe Ala Glu Ile Ala Ala Ala
                485                 490                 495

Ala Gly Ile Lys Ser Val Arg Ile Thr Asp Pro Lys Lys Val Arg Glu
            500                 505                 510

Gln Leu Ala Glu Ala Leu Ala Tyr Pro Gly Pro Val Leu Ile Asp Ile
        515                 520                 525

Val Thr Asp Pro Asn Ala Leu Ser Ile Pro Pro Thr Ile Thr Trp Glu
    530                 535                 540

Gln Val Met Gly Phe Ser Lys Ala Ala Thr Arg Thr Val Phe Gly Gly
545                 550                 555                 560

Gly Val Gly Ala Met Ile Asp Leu Ala Arg Ser Asn Ile Arg Asn Ile
                565                 570                 575

Pro Thr Pro
```